United States Patent [19]
Narodylo et al.

[11] Patent Number: 5,840,279
[45] Date of Patent: Nov. 24, 1998

[54] PHARMACEUTICAL POWDER CARTRIDGE WITH INTEGRATED METERING DEVICE AND INHALER FOR POWDERED MEDICAMENTS

[75] Inventors: Andre Narodylo, Linsengericht; Wolfgang Gottenauer, Bruchkobel; Joachim Goede, Hanau, all of Germany; Coenraad Lerk, Peize; Anne H. De Boer, Drachten, both of Netherlands

[73] Assignee: ASTA Medica Aktiengesellschaft, Dresden, Germany

[21] Appl. No.: 667,414

[22] Filed: Jun. 21, 1996

[30] Foreign Application Priority Data

Jun. 21, 1995 [DE] Germany .................. 195 22 415.9
Jun. 21, 1995 [DE] Germany .................. 195 22 416.7

[51] Int. Cl.⁶ .................................................. A61K 9/14
[52] U.S. Cl. .............................. 424/46; 424/45; 424/422; 424/434; 424/435; 222/3; 222/23; 222/402.1
[58] Field of Search ................... 424/45, 46, 422, 424/434, 435; 128/203.12, 203.15, 203.21, 203.23, 200.24; 604/57, 58; 222/3, 23, 402.1

[56] References Cited

U.S. PATENT DOCUMENTS

| | | | |
|---|---|---|---|
| 2,587,215 | 2/1952 | Priestly | 128/206 |
| 3,972,123 | 8/1976 | Black | 32/58 |
| 4,125,969 | 11/1978 | Easton | 51/320 |
| 4,274,403 | 6/1981 | Struve | 128/203.15 |
| 4,429,835 | 2/1984 | Brugger et al. | 239/338 |
| 4,570,630 | 2/1986 | Elliott et al. | 128/203.15 |
| 5,161,524 | 11/1992 | Evans | 128/203.15 |
| 5,284,133 | 2/1994 | Burns et al. | 128/200.23 |
| 5,301,666 | 4/1994 | Lerk et al. | 128/203.15 |
| 5,320,714 | 6/1994 | Brendel | 128/203.15 |
| 5,435,301 | 7/1995 | Herold et al. | 128/203.15 |
| 5,505,196 | 4/1996 | Herold et al. | 128/203.15 |

FOREIGN PATENT DOCUMENTS

| | | |
|---|---|---|
| 0079478 | 10/1982 | European Pat. Off. . |
| 0640354A2 | 9/1991 | European Pat. Off. . |
| 0546995A2 | 6/1993 | European Pat. Off. . |
| 846 770 | 8/1952 | Germany . |
| 3335745 | 10/1983 | Germany . |
| 3335745C1 | 10/1983 | Germany . |
| 4211475 | 6/1993 | Germany . |
| 4319514 | 12/1994 | Germany . |
| 91/6741 | 8/1991 | South Africa . |
| 94/2721 | 4/1994 | South Africa . |
| 94/4203 | 6/1994 | South Africa . |
| 2165159 | 10/1985 | United Kingdom . |
| 92/09322 | 6/1992 | WIPO . |
| 92/18188 | 10/1992 | WIPO . |
| 93/03782 | 3/1993 | WIPO . |
| 93/03785 | 3/1993 | WIPO . |
| 93/16748 | 9/1993 | WIPO . |
| 94/28957 | 12/1994 | WIPO . |
| 95/31237 | 11/1995 | WIPO . |

OTHER PUBLICATIONS

PCT International Search Report Oct. 1996 Application No. PCT/EP96/02396.

PCT International Search Report Mar. 1993 Application No. PCT/US92/07156.

*Primary Examiner*—Thurman K. Page
*Assistant Examiner*—Kathryne E. Shelborne
*Attorney, Agent, or Firm*—Baker & Daniels

[57] ABSTRACT

Pharmaceutical powder cartridge for powder inhalers for receiving a medicament depot for a large number of pharmaceutical powder doses, having an integrated metering device which comprises at least one metering cavity for receiving a predetermined quantity of a pharmaceutical powder, the integrated metering device being capable of being moved at least out of a filling position into an emptying position approximately transversely with respect to the flow direction of the pharmaceutical powder, and an inhaler for powdered medicaments, in which inhaler the medicament can be received by a patient by means of an air stream and which has a receptacle for such a pharmaceutical powder cartridge.

45 Claims, 8 Drawing Sheets

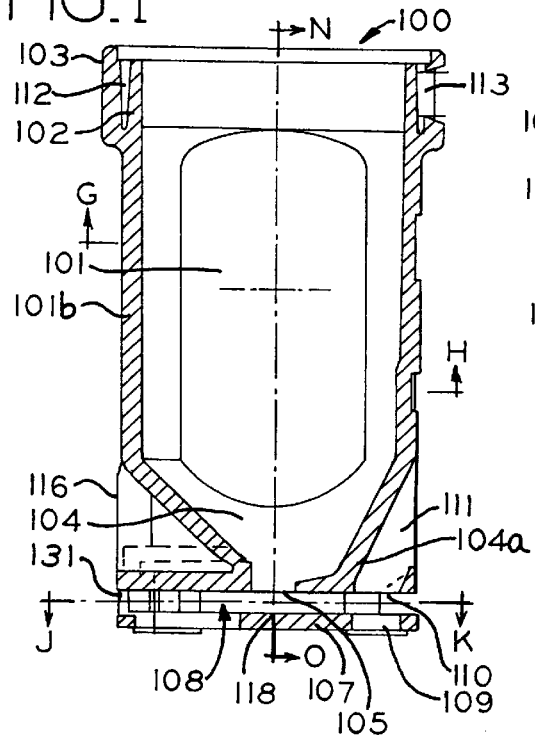
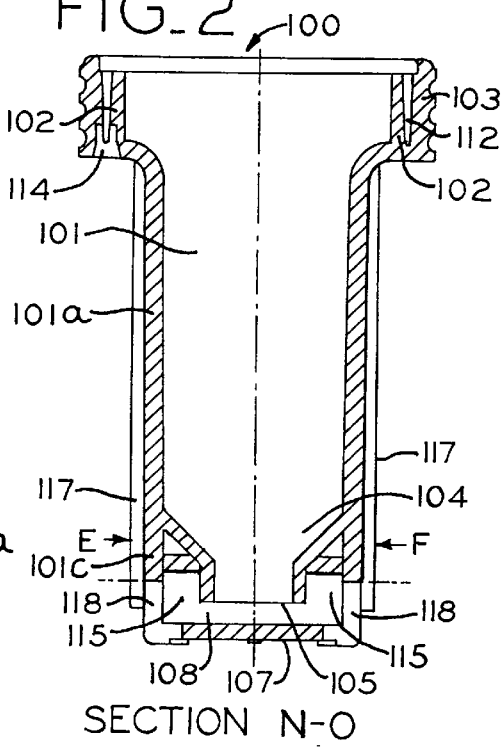
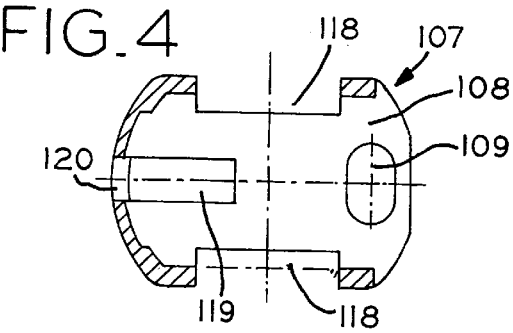
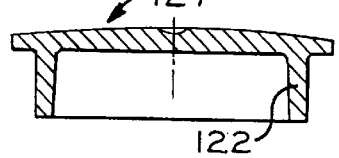
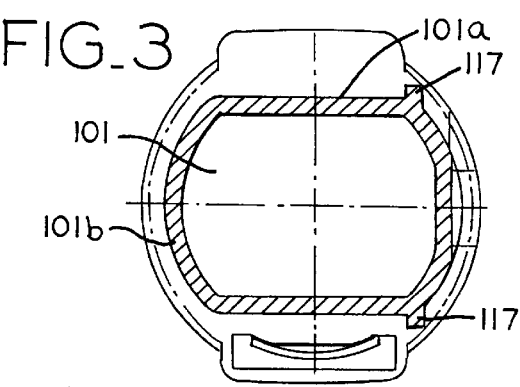
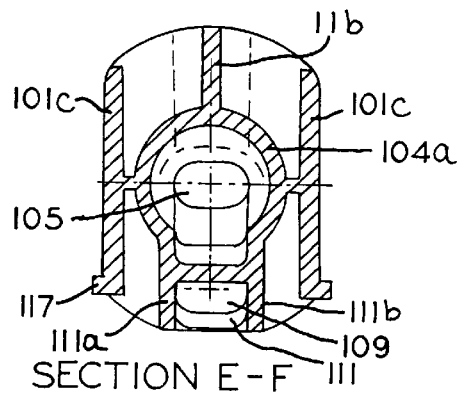

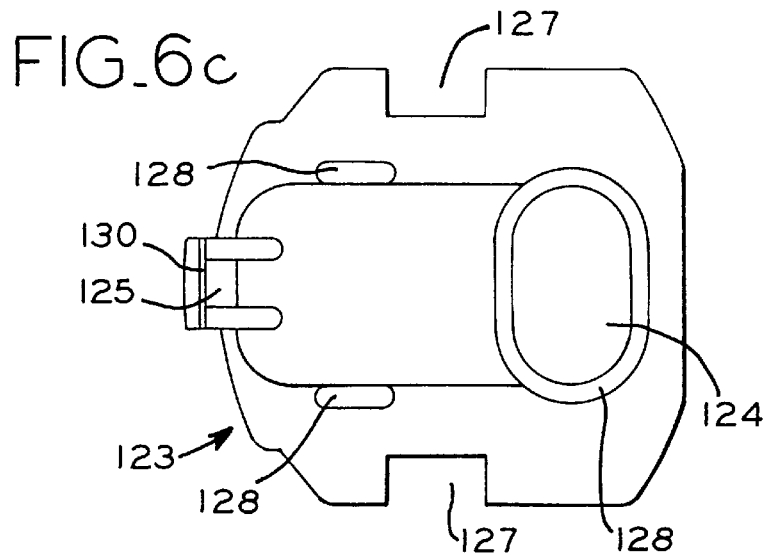
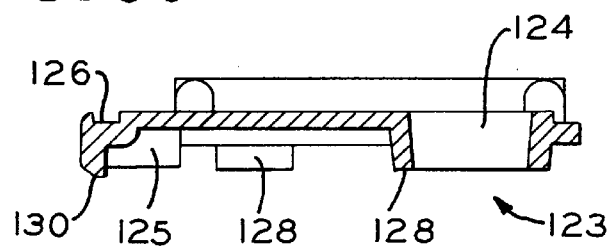
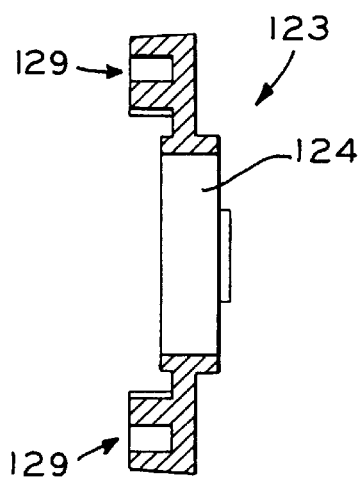
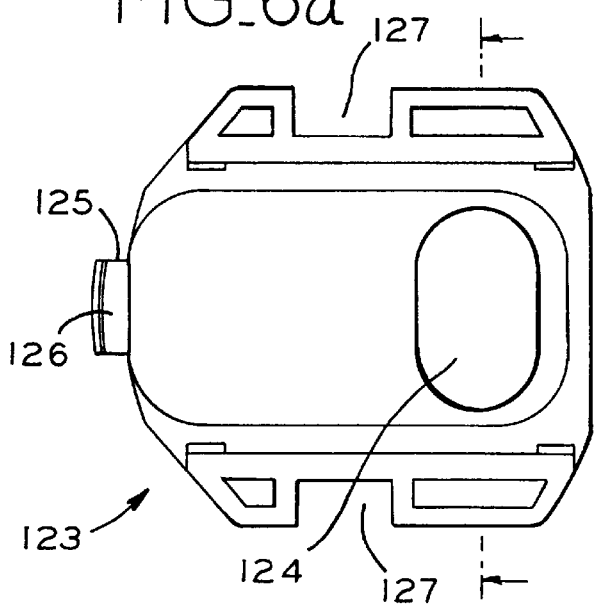

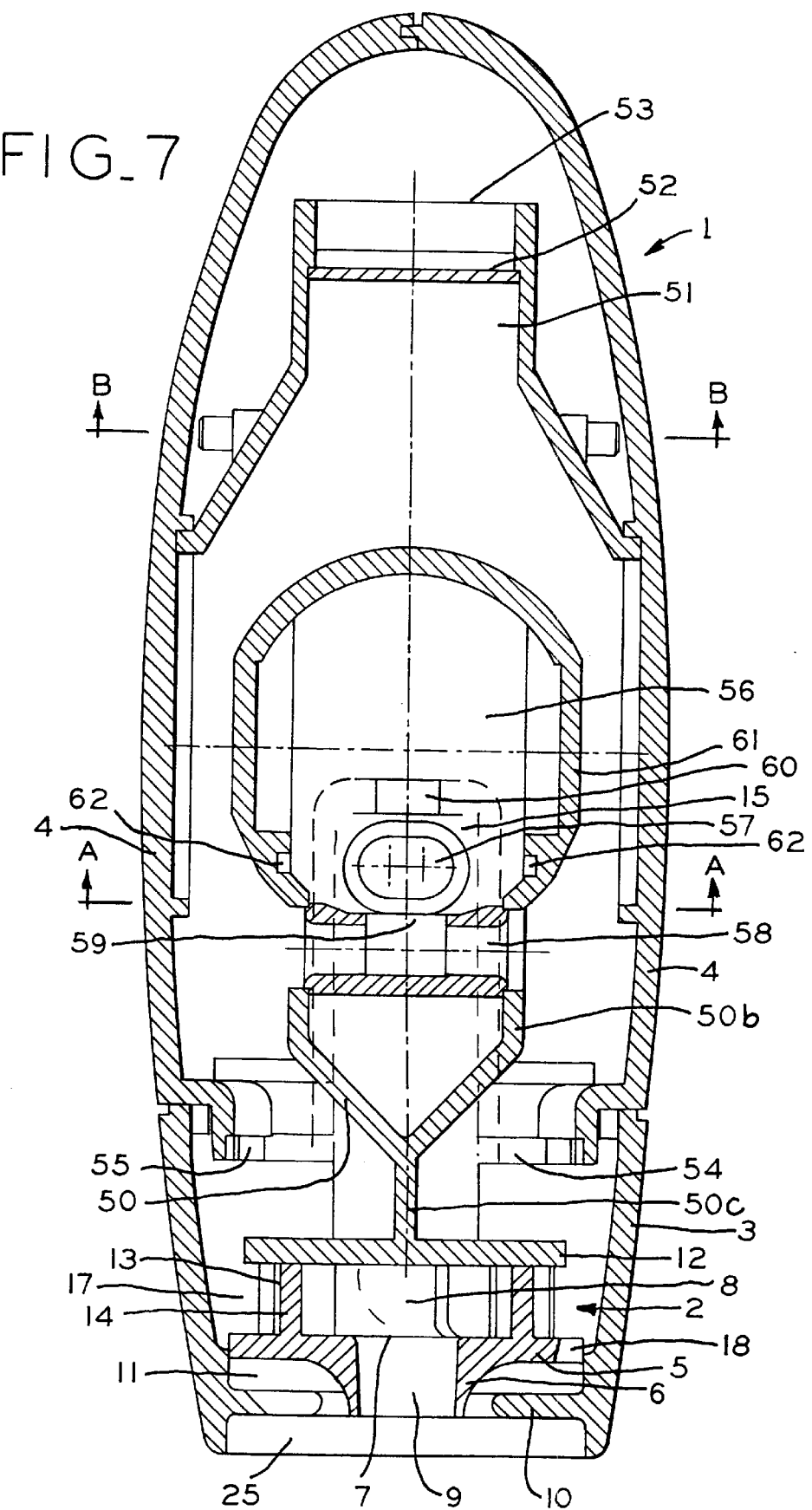
FIG_7

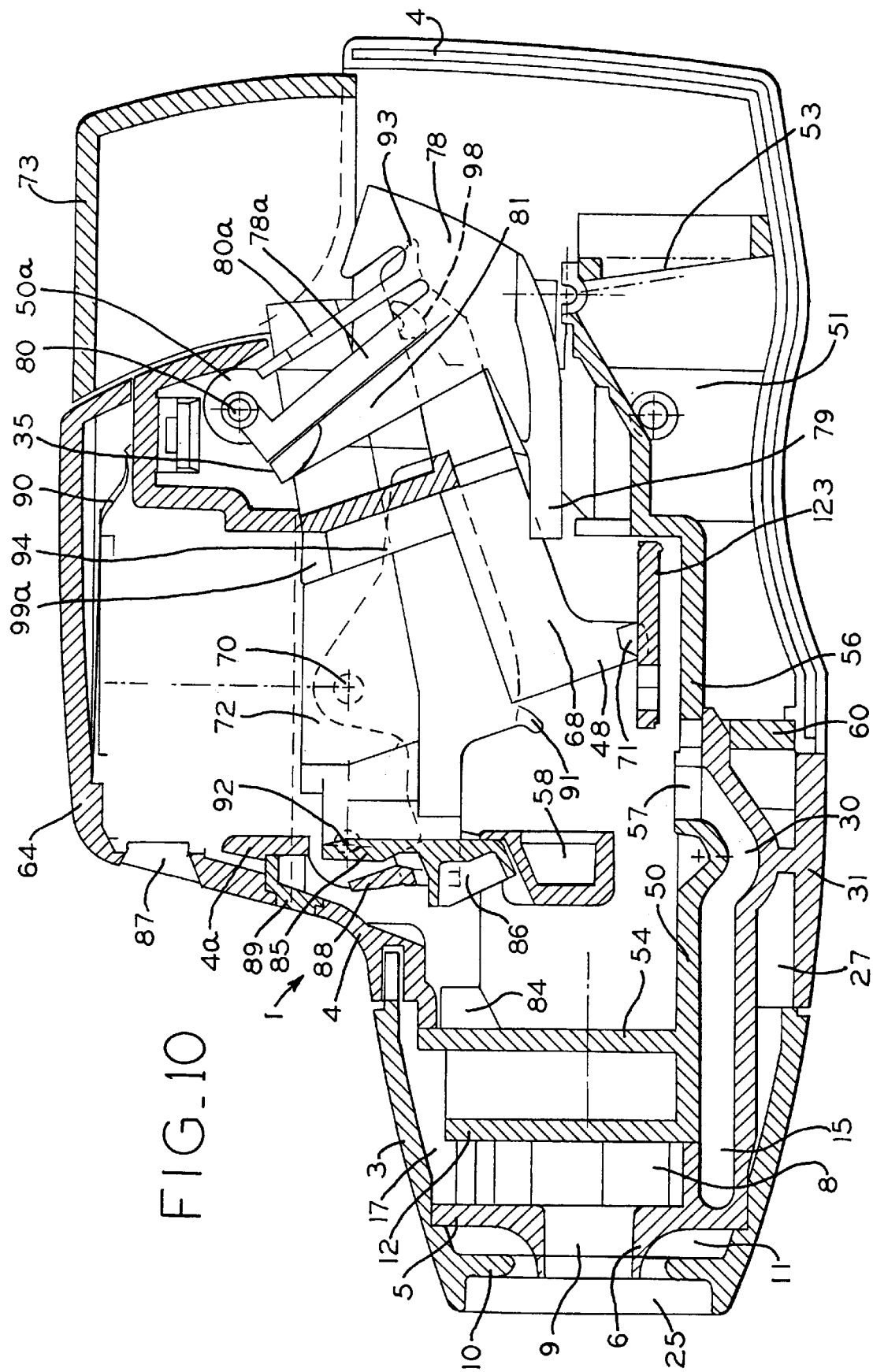
FIG_10

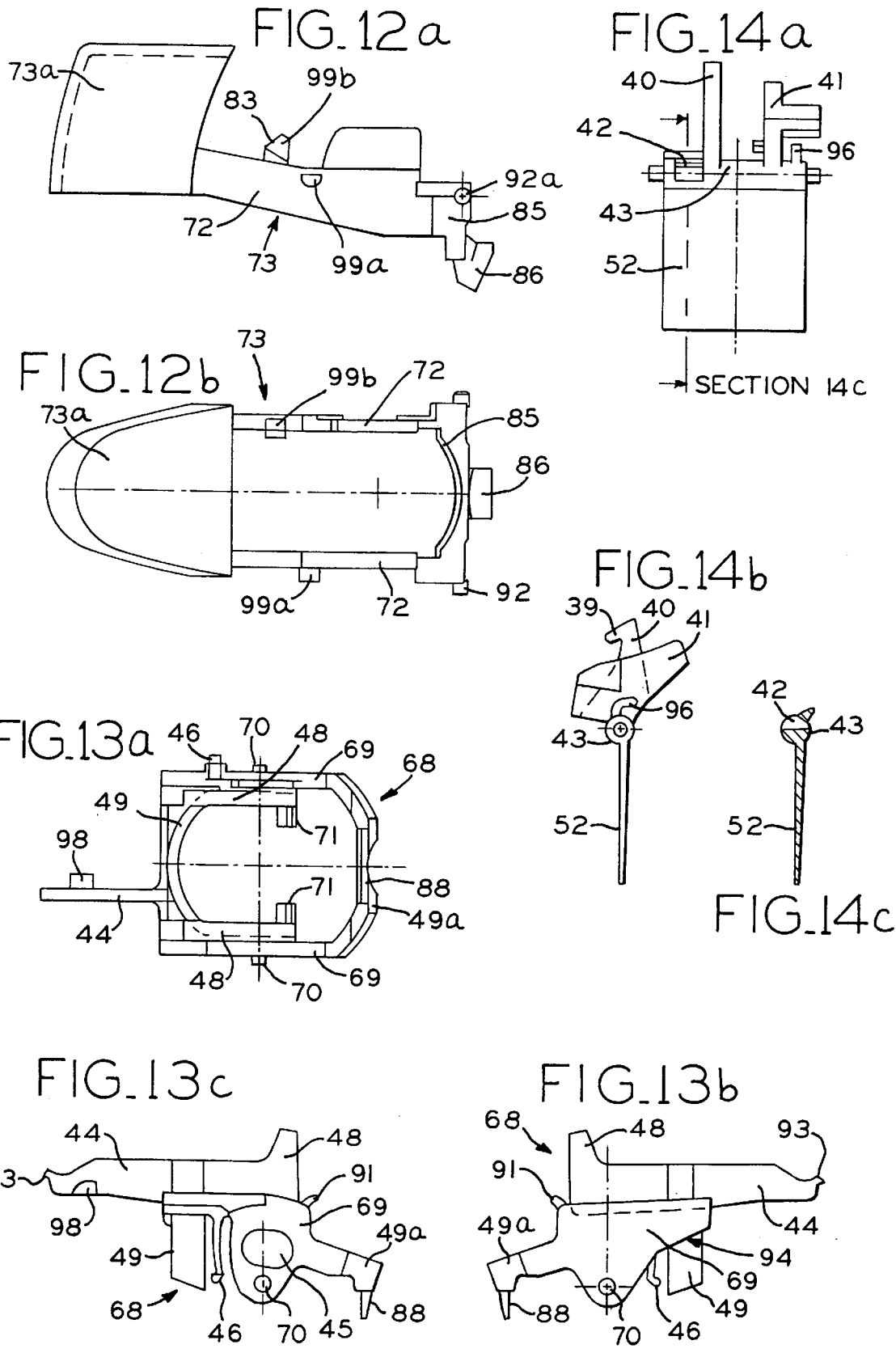

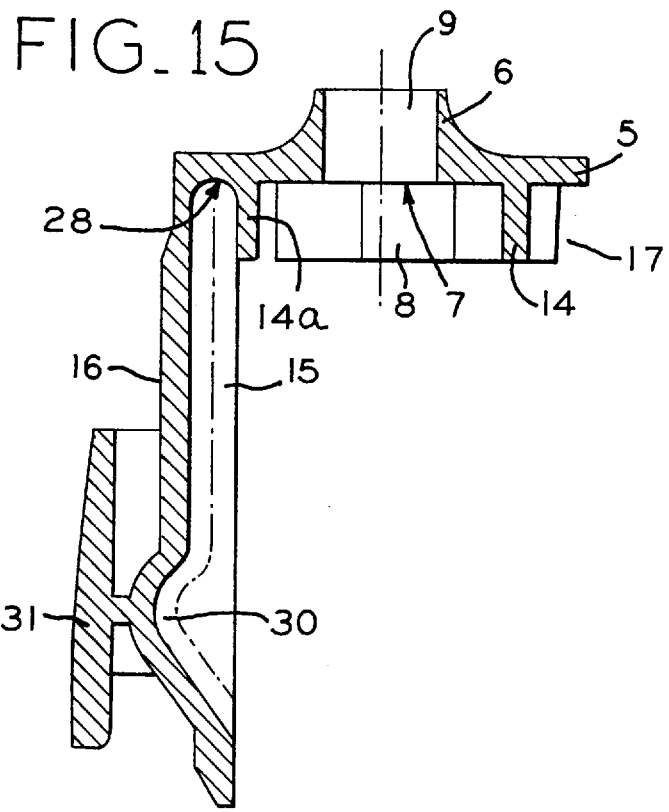
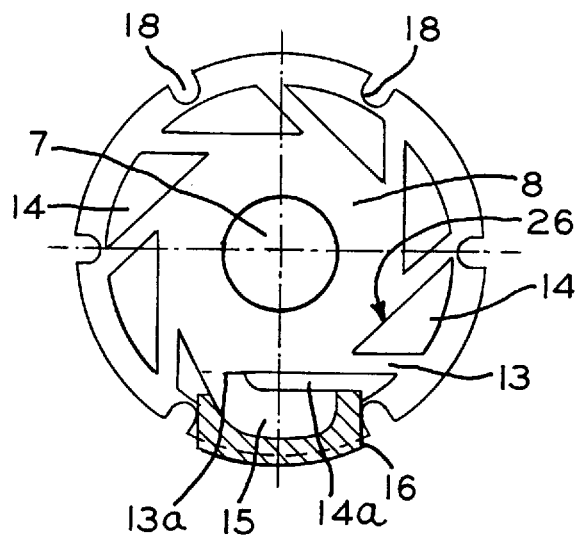

PHARMACEUTICAL POWDER CARTRIDGE WITH INTEGRATED METERING DEVICE AND INHALER FOR POWDERED MEDICAMENTS

FIELD OF THE INVENTION

The invention relates to a pharmaceutical powder cartridge for powder inhalers for holding a supply of medicament for a large number of doses of pharmaceutical powder, having an integrated metering device which comprises at least one metering cavity for holding a predetermined quantity of a pharmaceutical powder, and an inhaler for powdered medicaments, in which inhaler the medicament can be received by a patient by means of an air stream.

Such pharmaceutical powder cartridges and inhalers are used in particular for treating chronic disorders of the respiratory tracts. A typical field of application is the treatment of asthma sufferers. In such cases, a quantity of powdered medicament which is sufficient for a plurality of doses is packed into one pharmaceutical powder cartridge. The pharmaceutical powder cartridge is inserted into an inhaler which provides an air stream with medicament distributed in it for inhalation by the patient. When the inhaler is used correctly, the desired quantity of medicament thus passes into the bronchi and lungs of the patient. As a result of using a pharmaceutical powder cartridge instead of a reservoir container which is permanently arranged in the inhaler, the costs of such a treatment, in particular of a long-term treatment, are reduced since the inhaler can be used repeatedly.

PRIOR ART

WO-93/03782 discloses an inhaler for metering a preferably powdered inhalation preparation and for providing an inhalation stream. The described inhaler comprises a blocking device which prevents the medicament being metered if a sufficiently large air stream is not sucked in by the patient. The described inhaler comprises a replaceable pharmaceutical powder cartridge for holding a depot of medicament for [lacuna] integrated metering device. This metering device comprises a plunger which extends through a reservoir space of the pharmaceutical powder cartridge. In the region of its lower end, the plunger has a lateral metering cavity for receiving a predetermined quantity of the pharmaceutical powder. As a result of the pressing down of the plunger, the lower end of the plunger emerges from the cartridge and the metering cavity with the pharmaceutical powder moves into the region of an inhalation duct. As a result of the air stream produced by the patient, the pharmaceutical powder is distributed in the air stream and breathed in by the patient. In addition, a counting device for the inhaler is also proposed.

However, the described pharmaceutical powder cartridge has the disadvantage that the plunger with the metering cavity is moved through the supply of medicament. Therefore, as a result of the abrasive effect of the pharmaceutical powder there is the risk of the pharmaceutical powder cartridge becoming unsealed in the region of the bushing of the plunger and the pharmaceutical powder thus passing through in an uncontrolled fashion, or of the plunger becoming difficult to move and thus of reliable metering by the patient being impeded. In addition, owing to the bushings of the plunger and the necessary seals, the pharmaceutical powder cartridge is of relatively complicated design and is correspondingly expensive to manufacture. Furthermore, the described inhaler has the considerable disadvantage that the sucking in of an air stream by the patient and the activation of the metering plunger have to be coordinated. If the metering plunger is activated too early or too late in relation to the sucking in of the air stream, no pharmaceutical powder, or too little pharmaceutical powder, passes into the air stream and thus to the patient. In particular older patients or patients who are in a state of panic, as frequently occurs during asthma attacks, are frequently unable to cope with the necessary coordination.

DE-43 19 514 A1 and WO 94/28957 disclose an inhaler with a volumetric metering device. The described inhaler has a store, integrated into the inhaler, for a pharmaceutical powder, which store, with further elements of the inhaler, is impacted against further parts of the inhaler by releasing a pretensioned spring device. As a result of the impulse exerted when the store impacts against the pharmaceutical powder, said powder is to be compressed and the metering precision to be improved. In addition, the intention is to rule out multiple metering of the pharmaceutical powder. As a result of its complicated design, the described inhaler is relatively expensive to manufacture, and as a result of an integrated store for the medicament can only be used as a disposable device. As a result, the costs for a corresponding therapeutic treatment are substantially increased.

DE-42 11 475 A1 discloses an inhaler which contains a replaceable medicament magazine which contains a plurality of medicament doses in individual chambers. The individual chambers of the medicament magazine are emptied successively. The described inhaler also comprises a dispersing device in which the pharmaceutical powder is comminuted and distributed in the inhalation air stream in a cyclone chamber by means of kinetic energy. In addition, the air stream which is charged with the pharmaceutical powder is surrounded by an air stream which is free of pharmaceutical powder. The intention is to prevent the pharmaceutical powder being deposited in the mouth or throat region. Although the inhaler described is intended for repeated use, owing to its complicated design it is relatively expensive The disposable medicament magazine is also relatively expensive since it comprises a large number of individual parts and is difficult to fill because of the large number of medicament reservoir chambers.

SUMMARY OF THE INVENTION

The invention is therefore based on the object of providing a pharmaceutical powder cartridge and an inhaler with which the costs for the therapeutic use of a medicament are reduced. In addition, simple and reliable operation is to be made possible even for patients with poor coordination and such patients who are under extreme stress.

This object is achieved according to the invention by means of a pharmaceutical powder cartridge of the type mentioned at the beginning in which the integrated metering device comprises a metering slide which can be moved at least out of a filling position into an emptying position approximately transversely with respect to the flow direction of the pharmaceutical powder. The object is also achieved by an inhaler of the type mentioned at the beginning which comprises a receptacle for such a pharmaceutical powder cartridge and an inhaler with an optical display device for displaying the direct discharge of a medicament dose.

The pharmaceutical powder cartridge according to the invention can be manufactured particularly simply and economically so that it permits particularly cost-effective packaging of a depot of medicament and at the same time can be disposed of in a hygienically particularly advantageous way after a single use. After the pharmaceutical powder cartridge has been replaced, the inhaler according to the invention can be used again repeatedly and is also particularly easy and safe to operate even for elderly patients.

For a particularly good handling of the pharmaceutical powder cartridge before insertion into an inhaler it is advantageous if the metering slide can also be moved into a transportation position, in particular if the metering slide is fixed in the transportation position by spring-elastic means. If the medicament cartridge according to the invention is to be removed from an inhaler although it is not yet completely emptied, it is expedient if the medicament cartridge has on its underside a viewing window via which the position of the metering slide can be checked. In particular for patients for whom a medicament which is packed into the pharmaceutical powder cartridge is of vital importance, it is expedient if the pharmaceutical powder cartridge according to the invention is distinguished by a display device for the quantity of pharmaceutical doses which have been removed or which remain in the pharmaceutical powder cartridge, the display device for the quantity of medicament doses which have been removed or which remain being integrated into the upper edge region of the pharmaceutical powder cartridge.

An inhaler according to the invention which comprises a device for activating the metering slide of the integrated metering device of a pharmaceutical powder cartridge according to the invention, moving it at least a filling position into an emptying position, and a securing device for preventing the metering slide from returning into the filling position before the medicament dose is removed from the inhaler, is particularly well protected against incorrect operation, in particular if the inhaler also comprises a safety device which largely prevents the formation of an air stream for the removal of the medicament if the metering slide has not yet completely reached the emptying position. In particular for patients for whom the use of the medicament contained in a pharmaceutical powder cartridge according to the invention is of vital importance, it is particularly reassuring if an inhaler according to the invention comprises a visual display device for displaying that a medicament dose has been discharged, in particular if the inhaler comprises a device for reading, from outside the inhaler, the display device of a pharmaceutical powder cartridge according to the invention which has been inserted into the inhaler. It is particularly user-friendly here if the visual display devices and the device for reading the display device of a pharmaceutical powder cartridge which has been inserted into the inhaler are arranged on the inhaler in such a way that they are located in the field of vision of a patient when the said patient holds the inhaler in its position of use for inhaling.

Further expedient and advantageous features of the invention are claimed in the further subclaims.

BRIEF DESCRIPTION OF THE DRAWINGS

The structural design according to the invention of the pharmaceutical powder cartridge with metering device integrated therein, and of the powder inhaler which contains the means for activating the metering device, and the specific dispersing device, is described in greater detail with reference to the figures.

FIG. 1 shows the pharmaceutical powder cartridge in a vertical section.

FIG. 2 is a vertical section through the powder cartridge along line N–O in FIG. 1.

FIG. 3 is a section along the line G–H in FIG. 1 and shows a cross section through the pharmaceutical powder cartridge viewed from above.

FIG. 3a is a section along line E–F in FIG. 2 and shows a cross section through the powder cartridge in its lower region above the metering device.

FIG. 4 shows a section along the line J–K in FIG. 1.

FIG. 5 is a cross section through the lid of the pharmaceutical powder cartridge.

FIG. 6a to d show sectional views of the metering slide, longitudinal sections and cross sections viewed from above, from below and from the side.

FIG. 7 is a horizontal longitudinal section through the powder inhaler, viewed from above, without a pharmaceutical powder cartridge inserted.

FIG. 10 is a vertical longitudinal section through the powder inhaler without a powder cartridge inserted but with a schematically represented metering slide of the metering device integrated into the powder cartridge, in the metering position.

FIGS. 12a and b show the metering button from the side and from above.

FIGS. 13a to c show views of the metering lever from both sides.

FIGS. 14a to c show the valve flap with its locking elements in various views, (c)=section.

FIG. 15 shows a longitudinal section through the metering device with the powder duct.

FIG. 16 shows a cross section through the metering device with a view of the front wall of the chamber from the chamber interior.

DESCRIPTION OF PREFERRED EMBODIMENTS

Figure 9:
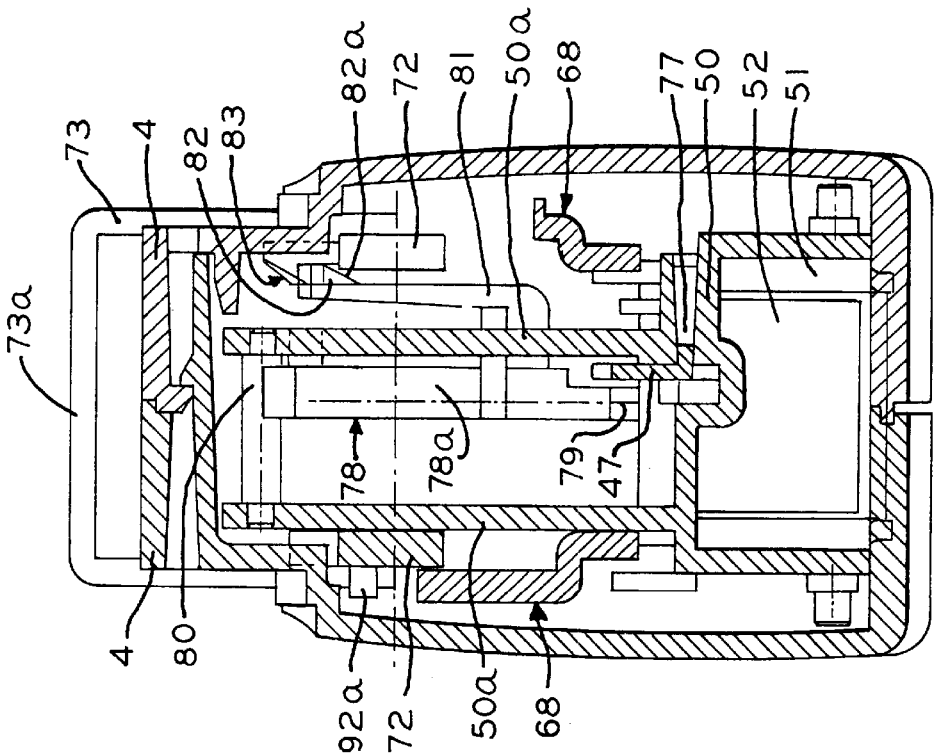
FIG. 9 is a section along line BB in FIG. 7 and it shows the cross section of the powder inhaler, viewed from the front, in the rear part of the housing.

The powder inhaler which is configured for continuous use is designed in such a way that the insertable cartridge can be inserted without difficulty in a specific position by the user after a lid has been removed from the powder inhaler. Furthermore, the powder inhaler according to the invention has a dispersing device for the pharmaceutical powder, which dispersing device is easily accessible and can be cleaned easily by removing a mouthpiece arranged on the front side, and is connected via a powder duct to the metering device of the pharmaceutical powder cartridge within the inhaler housing.

The pharmaceutical powder cartridge according to the invention, which can be inserted into an inhaler, has an elongated reservoir space, which can be closed by a lid which can be inserted into the upper edge, for a plurality of pharmaceutical powder doses, the side wall of said reservoir space tapering in the lower region of the cartridge in a funnel shape to an outlet opening, it being possible to connect the outlet opening to a metering cavity of the metering device and the integrated metering device having a cartridge base and a metering slide duct which is arranged between the cartridge base and the lower end of the reservoir space and whose ends are preferably aligned approximately with the outer circumference of the cartridge, a metering slide which can move forward and backward horizontally, with a metering cavity constructed in the proximity of its end, being arranged in the metering slide duct, there being in the cartridge base a discharge opening which is laterally offset with respect to the outlet opening of the reservoir space and which is aligned with a purging air opening in the upper wall of the metering slide duct, and the purging air opening forming the end of a purging air duct which is arranged outside the side wall of the cartridge.

The pharmaceutical cartridge can have a medicament-specific bulge in the cross section. The cross section of the functional carrier region is of corresponding construction in order to receive the cartridge.

Preferably, the pharmaceutical powder cartridge has an integrated display device for medicament doses which have been removed. The said display device can be integrated into the upper edge. In such a case, the powder inhaler also contains the means necessary for activating the display device.

The display device of the pharmaceutical powder cartridge has a web-shaped upper outer edge which coaxially surrounds the upper edge of the cartridge at a distance and is offset outward from the upper edge so that, between the outside of the upper edge of the cartridge and the inside of the outer edge, an annular gap which is open at the top is formed before the insertion of the cartridge lid. In the outer edge there is a viewing window which makes it possible to see the position of a film strip which is inserted into the annular gap and provided with marks and whose lower edge is constructed as a row of teeth.

Instead of a film strip, a plastic ring which has marks and whose lower edge is constructed as a row of teeth may also be used. Such a ring is easy to manufacture by means of injection molding.

In the shoulder which connects the outer edge to the side wall of the cartridge, there is an offset recess which extends into the annular gap, for the engagement of a toothed wheel in order to permit horizontal rotation of the film strip in the annular gap about the longitudinal axis of the cartridge. The film strip or plastic ring is provided with marks which indicate the number of medicament doses removed from the metering device of the cartridge and thus make it possible to indicate promptly an imminent end of the supply of pharmaceutical powder. For the practical use of the powder inhaler, it is sufficient if the imminent end of the supply of pharmaceutical powder is promptly indicated to the user automatically by a suitable marking on the film strip or plastic ring. This can be achieved for example by means of a colored marking which increases in size or by numbers or bar marks at different intervals. It is sufficient if the film or the ring is moved on by a specific distance whenever a plurality of removals have occurred.

So that the display device can also be read at the pharmaceutical powder cartridge inserted into a powder inhaler, the powder inhaler according to the invention preferably has an opening in the lid, which opening is aligned with the opening in the outer edge of the inserted cartridge. The film strip or the plastic ring is positioned in the annular gap before or after the cartridge is filled with pharmaceutical powder, and the powder cartridge is then closed with a lid.

Therefore, the offset outer edge is preferably constructed to be higher than the upper edge of the cartridge and the lid has a connector element whose outer diameter corresponds to the inner diameter of the upper edge so that after the insertion the lid is held by a snug fit of the edge of the cartridge. The outer edge of the lid which extends outward from the connector element extends over the upper edge and the annular gap into a shoulder on the inside of the outer edge and is arranged countersunk within the outer edge of the cartridge. As a result, unauthorized opening of the powder cartridge without destroying or damaging the lid is made considerably more difficult so that the medicament manufacturer can comply with his guarantee obligations when bringing the powder cartridge onto the market.

The metering device is integrated into the lower region of the pharmaceutical powder cartridge and the metering slide duct preferably has a U-shaped cross section and is open at one longitudinal side. The legs of the U, which form the side walls of the duct, have recesses which permit operating means to engage on the metering slide arranged in the metering slide duct in order to displace the metering slide horizontally. The upper duct wall of the metering slide duct between the legs of the metering slide extends from the outside of the funnel of the powder cartridge. The correspondingly constructed meter slide has a U-shaped cross section and recesses on the outside of the legs for activation means to engage through the recesses in the side walls of the metering slide duct. In order to protect the metering slide against falling out of the metering slide duct after the cartridge has been installed, the metering slide has at the end facing away from the metering cavity a protruding element with a downwardly directed stop for engaging in a corresponding slit which extends in the longitudinal direction of the cartridge base and into which the protruding element locks, with a stop, on first being pushed in. In order to secure the metering slide for transportation, the protruding element of the metering slide can have on the upper side a keyway for a lug, facing the metering slide duct, in the upper wall of the metering slide duct, to engage in. As a result of the fact that the metering slide can move with means which engage from the outside, the locking connection between the lug and keyway can be designed in such a way that a relatively small force is sufficient to release the lock because engagement in the recesses of the metering slide during the transportation and storage of the powder cartridge is not to be expected under normal circumstances.

The cartridge lid, the metering slide and the pharmaceutical cartridge with the integrated metering device without the metering slide can be manufactured as separate parts from medically acceptable thermoplastic. Particularly suitable thermoplastics are those which can be shaped by means of injection molding, for example polyethylenes, polypropylenes, polycarbonate, polyurethane, polyacrylate, polystyrene, acrylonitrile butadiene styrene copolymers. However, it may also be advantageous to use different plastics for individual parts, for example the cartridge and metering slide.

The construction, according to the invention, of the integrated metering unit with a metering slide which can move forward and backward has proven operationally reliable for the number of usual medicament doses of a powder supply which may constitute 200–300 doses, in exceptional cases even up to 500 doses, within a cartridge. A cartridge base which is relatively thin construction and which is connected to the upper lid of the metering powder duct and to the underside of the cartridge at a plurality of points in order to form the metering slide duct, avoids the metering slide becoming clamped tight in the metering slide duct owing to a spring effect. In order to avoid the metering slide tilting in the metering slide duct during operation, said metering slide is guided on both sides and activation fingers engage on the metering slide simultaneously from both sides.

The powder inhaler which is suitable for the pharmaceutical powder cartridge according to the invention has a housing which, if appropriate, has one or more air inlet openings and has on the front side a mouthpiece for inhaling, which can be removed from the housing. There is an opening which can be closed by a lid and has the purpose of inserting a pharmaceutical powder cartridge with the metering device integrated therein, and a metering button on the upper side of the housing. Arranged within the housing and the mouthpiece are:

(1) a functional carrier with horizontal and a plurality of vertical elements for receiving means which act on a pharmaceutical powder cartridge after its insertion into the powder inhaler and its metering device and (2) a horizontal receiving surface of the functional carrier for the insertable pharmaceutical powder cartridge, the receiving surface having a passage opening which is aligned with the discharge opening of the metering device which is integrated into the pharmaceutical powder cartridge;

(3) a dispersing device arranged in the hollow cylindrical or truncated cone-shaped mouthpiece, for dispersing powdered medicament doses in the air stream which is sucked in through a central opening in the mouthpiece during inhalation, the metering device being connected by a powder duct to the passage opening in the supporting surface of the functional carrier and the dispersing device having means in order to branch off from the dispersing air stream fed to the dispersing device a powder-free partial air stream which surrounds, as a surrounding air stream, the air stream which leaves the dispersing device and is charged with powder, (4) an impulse transmitter which is coupled to first vertical elements of the functional carrier which are arranged parallel to one another at a distance, for the purpose of supplying a mechanical impulse to an inserted powder cartridge,
(5) a metering lever which is coupled to a second vertical element with two surfaces of the functional carrier which are arranged parallel to one another at a distance, for the purpose of activating the metering device, integrated into the pharmaceutical powder cartridge, for pharmaceutical powder,
(6) parts of the metering button which extend through the housing and whose front ends are coupled to other points of the surfaces, arranged parallel to one another at a distance, of the second vertical element of the functional carrier, and there are means which engage on the parts on the metering lever in order to pivot the metering lever about its pivotal center, and there are means for activating the impulse transmitter,
(7) further elements of the functional carrier at the rear end of its horizontal part which form a valve chamber within the housing, with an opening in the rear part of the housing interior, which opening can be closed by a valve flap which is coupled to functional carrier elements, the valve chamber being connected to the dispersing device via an air duct and a partial air duct branching off from the air duct to the metering device of the pharmaceutical powder cartridge in order to lead a partial air stream through the metering device to the powder duct, in order to convey a medicament dose out of the metering device into the dispersing device.

The quantity of the partial air stream which is fed through the duct of the metering device which branches off is determined by the free cross sections of the ducts and the latter are selected such that a quantity of air which is sufficient for transporting the medicament dose out of the metering cavity of the metering slide through the powder duct as far as the dispersing device is branched off from the total air stream which is produced by sucking in. As a rule, approximately 25% of the sucked in air is sufficient for this. However, higher proportions may also be used.

The pivotable valve flap is held in the closed position by means of a spring and can be pivoted counter to the spring force and effect by the air stream produced during inhalation by sucking in and can clear the opening of the valve chamber to the housing interior.

In order to prevent premature inhalation before the metering is activated, the pivotable valve flap is preferably locked until the metering procedure in the processing device is concluded.

In the closed position, the pivotable valve flap holds the metering lever tight after the metering position has been reached and does not release said metering lever again until after the inhalation procedure so that it jumps back into the initial position (filling position) together with the metering slide.

This is made possible by the fact that the valve flap has on its upper edge a shaft with outwardly directed bearing journals which engage in bearing bushes on functional carrier elements which form the valve chamber walls, and in the shaft there is a recess with a blocking edge in which a locking element of the metering lever engages when the metering procedure is concluded.

In order to prevent double dosage or repeated dosages during which the metering lever is moved forward and backward repeatedly between the initial position, in which the metering cavity is located in the filling position, and the limit position in which the metering cavity is located in the emptying position (metering position), there is a further locking means between the metering lever and valve flap, which locking means prevents the metering slide being able to be moved a second time into the filling position by the metering lever without inhalation. For this purpose, next to the recess an arm extends upward from the shaft, on the end of which arm there is a hook with a blocking edge in which a further locking element of the metering lever can engage.

In order to facilitate the assembly of the powder inhaler and to avoid attachment means which are visible from the outside, the housing is preferably composed of two half shells with a tongue/groove joint. In order to attach the half shells to the functional carrier and to fix it within the housing, it is preferred to provide inwardly directed locking elements or sprung catch elements which engage in corresponding openings of the functional carrier and its elements, and connect the housing shells to the functional carrier. On the upper side of the powder inhaler it is preferred to provide additional direct locking connections between the two half shells by means of elements which engage in one another.

The rear part of the surface of the powder inhaler is of flatter construction than the front part because the latter has to be of sufficiently high construction to receive the pharmaceutical powder cartridge. The flatter construction of the rear part of the housing of the upper side permits a metering button for triggering the metering process to be arranged in this region, said metering button having parts which extend as far as the pivotal center of the button which is arranged within the housing. Preferably, the button has at the edge a downwardly directed, circumferential edge which extends into a corresponding gap on the upper side of the housing. In this way, the intermediate space between the upper side of the metering button in its initial position and the upper side of the housing is closed and it is made more difficult for the metering button to tilt during activation.

In order to fix the pharmaceutical powder cartridge in the correct position in the powder inhaler, the second vertical elements of the functional carrier are constructed as a vertical shaft whose inner cross section is matched to the outer contour of the powder cartridge to be inserted, and between the side walls of the shaft and the side walls of the powder cartridge there is still space for operating elements, such as the metering lever and the parts of the metering button which extend from the upper side of the housing.

A sliding lid is provided for closing the opening for the cartridge and securing the cartridge. The sliding lid is constructed as a shell and engages in a bayonet-like manner about the part of the powder cartridge which protrudes into the upper edge of the opening. In order to fix the sliding lid to the housing, integral spring-elastic regions are provided on the side of the lid, which regions are provided with catch lugs and engage in corresponding regions of the two housing shells. In the interior of the sliding lid there is a leaf spring which acts on the lid of the inserted powder cartridge and holds the cartridge in place.

At the edge of the sliding lid there is a viewing window which is arranged aligned with the viewing window of the display device of the powder cartridge. It is especially preferred to arrange the window on the front side of the lid because, as a result, the filling level of the powder cartridge or the number of doses which have been removed can be easily determined visually by the user before and after use.

In order to indicate to the user that the powder inhaler is ready for inhalation after conclusion of the metering procedure triggered by the metering button, there is a further window, preferably above the mouthpiece, which window is formed by cutouts in the two housing shells and the sliding lid, in the region of which an indicating symbol which is connected to the activation means, arranged in the powder inhaler, for the metering device indicates, depending on the position of the activation means, that the inhaler is ready for inhalation or not.

In order to activate the metering device integrated into the pharmaceutical powder cartridge, a pivotable metering lever is coupled to the functional carrier element which surrounds the powder cartridge.

The metering lever has two lateral surfaces at a distance from one another, the ends of which surfaces are connected to one another by bridges forming a ring which surrounds the powder cartridge at a distance. Bearing journals extend outward from the lateral surfaces, in their upper regions, in bearing holes in the side walls of the second vertical element of the functional carrier so that, owing to its annular diameter which is larger than the diameter of the powder cartridge, the metering lever is mounted so as to be capable of pivoting in the longitudinal direction of the powder inhaler. The metering lever has means for engaging in the metering device which is integrated into the lower part of the powder cartridge, and means for locking to the valve flap.

The means on the metering lever for engaging in the metering device are fingers which extend from arms which are offset laterally into the ring against the lateral surfaces and extend downward, directed one toward the other, through recesses in the side walls of the metering slide duct into recesses in the side edges of a metering slide which is arranged so as to be capable of moving forward and backward in the metering slide duct of the metering device. In the initial position, the metering slide is located in a so called filling position in the metering device, in which filling position the metering cavity of the metering slide is located underneath the opening in the funnel of the powder reservoir cartridge and at the same time the fingers on both arms of the metering lever engage through the side wall of the metering chamber duct in the recesses in the side edges of the metering slide.

In order to promote the filling of the metering cavity with the desired quantity of pharmaceutical powder, there is a so called impulse transmitter with a hammer element in the powder inhaler, said hammer element striking against a web on the outside of the wall of the powder cartridge when the metering button is activated. This mechanical impulse is transmitted to the flowable pharmaceutical powder so that it flows out of the funnel into the metering cavity under the force of gravity and fills said metering cavity in a reproducible manner. This impulse takes place before the metering slide is moved away out of the filling position. The impulse transmitter is arranged in the rear part of the housing of the powder inhaler. The initial vertical elements of the functional carrier are the arms which extend upward from the horizontal part of the functional carrier, behind the supporting surface, and have bearing bushes at their upper ends for receiving the bolts on the shaft of the impulse transmitter. The impulse transmitter has a lever with a hammer element at the lower end and a shaft at the upper end, said hammer element extending in the direction of the longitudinal axis of the powder inhaler.

Furthermore, on one side of the lever there is a transverse spring element (spring elastic region) which cannot be deflected in the direction of movement of the lever of a load but can be deflected transversely thereto. On the opposite side of the lever a drive spring of the impulse transmitter is molded on.

One of the rockers of the metering button within the housing has an upwardly extending projection with a driver which also projects beyond the rocker toward the inside and serves to activate the impulse transmitter. The distance between the projection and the pivotal center of the metering button is selected to be such that the engagement of the projection on the impulse transmitter takes place when the metering button is pressed in only slightly. As a result of the action of the projection on an working surface of the transverse spring element of the impulse transmitter, the latter is pivoted away from the powder cartridge and the molded on spring of the impulse transmitter is tensioned. As a result of the rotation of the metering button, its projection slips off the working surface on the transverse spring element after the tensioned state of the molded on spring is reached, and the impulse transmitter is pivoted against the powder cartridge owing to the spring tensioning and strikes against it. In order to increase the mass, the impulse transmitter is preferably reinforced in the lower region of the lever.

As a result of the fact the transverse spring element can be deflected laterally, when the metering button returns into the initial position the projection can move laterally past the working surface on the transverse spring element and can engage on the working surface of the projection again when the metering button is next pressed in. In order to facilitate this return movement, the projection has an oblique surface over which the transverse spring element slides during the lateral deflection.

After the metering cavity is filled, the metering lever is pivoted and it moves the metering slide into a center position in which the metering cavity is located between the filling opening on the funnel and the emptying opening on the underside of the metering slide duct in the base of the powder cartridge. In order to rule out incorrect operation during metering, the metering slide must be prevented from returning into its initial position before the metering cavity has been emptied.

For this purpose, the metering lever has means for locking to the blocking edge of the hook on an arm which extends upward from the shaft of the valve flap. These means are an arm which extends rearward from the ring of the metering lever, underneath the said metering lever, and which has a hook-shaped latch which is attached to one side at a distance from the end of the arm and whose effective surface is positioned such that, in conjunction with the valve flap arm, it brings about permanent locking of the closed valve flap to the metering lever and at the same time causes the metering slide to be fixed by means of the arms of the metering lever and its fingers which are engaged with the metering slide. This mechanical blocking device cannot be released by sucking air through the powder inhaler, on the contrary the locked valve flap makes inhalation more difficult such that it is not possible to produce a sufficient inhalation air stream by sucking. The metering lever can only be moved on out of this position and into its limit position by means of the metering button, in which limit position the fingers on the arms have moved the metering slide into the emptying position in which the metering cavity is aligned on the upper side with the ventilation duct and on the lower side with the opening of the powder duct in the receiving surface of the powder cartridge.

In this position too, it is necessary to lock the metering lever and fix the metering slide until the inhalation procedure in order permit the dose of pharmaceutical powder to be transferred from the metering cavity into the dispersing device through the powder duct. For this purpose, there is a catch hook or limit catch at the end of the metering lever, which catch hook engages in a recess in the shaft of the valve flap with a blocking edge in this position of the metering lever. The lower edge of the arm on the metering lever is curved in such a way that the engagement of the hook in the recess of the shaft of the valve flap is released when the valve flap moves. The limit catch connection of the metering lever locks said metering lever to the shaft of the valve flap without the valve flap still having to be simultaneously blocked from moving. The valve flap is merely held in closed position by means of a weak tension spring. Its spring force can be overcome by the air stream produced during inhalation by sucking so that the valve flap is pivoted into the valve chamber by the air stream. The release of the locking connection of the metering lever to the shaft takes place with a slight delay which is however sufficient to ensure that, by the time the locking of the metering lever has been released, the dose of medicament is conveyed out of the metering cavity into the powder duct and through the latter to the dispersing device.

The metering lever has on one lateral surface a lug for hooking in a restoring spring, the other end of the restoring spring being fixed to a hook which is arranged on a horizontal element of the functional carrier which forms the cover of the valve chamber. The force of the restoring spring of the metering lever is sufficient to pull back the metering lever into the initial position after the release of the limit lock with the locking edge on the shaft of the valve flap so that a renewed metering procedure is possible after the inhalation has been concluded.

In order to indicate externally the limit position of the metering lever and the readiness of the metering cavity to be emptied, the bridge which connects the front ends of the lateral surfaces of the metering lever is constructed as a foot for an indicating symbol which extends upward therefrom and, in this position of the metering lever, is located behind an opening which is arranged on the front side of the housing. As soon as the metering lever is pulled back into its initial position by the restoring springs during the inhalation procedure, the indicating symbol disappears again from the window region.

During its movement, the metering lever also acts on the drive device for the display device in the powder cartridge.

In order to make this possible, one of the lateral surfaces of the second vertical element of the functional carrier has a bearing hole for a toothed pinion for activating the display device, integrated into the upper edge of the powder cartridge, for doses of the medicament which have been removed. This drive device is arranged between the housing wall and a side wall of the shaft and has means for activating the display device, integrated into the upper edge of the powder cartridge, for doses of medicament which have been removed from the powder cartridge. These means for activating the display device are an intermediate wheel which engages directly into the display device and is mounted on a journal which protrudes with respect to the upper edge of the housing and is driven by the abovementioned pinion with a smaller number of teeth, and the pinion also having a wheel which is offset laterally on the axle with respect to the housing wall and has a larger outer diameter and transportation toothing. When the metering lever is activated, said wheel is incrementally rotated further by a spring arm which is provided on the metering lever and has a lug at the end. The transmission ratio is selected such that for each metering procedure a small displacement is brought about in the display device of the powder cartridge of the film strip which is provided with marking and that the limit position of the display device is reached after the cartridge has been emptied.

A further spring arm is located in the same side of the second vertical element of the functional carrier and likewise engages in the transportation toothed wheel with the purpose of permitting rotation only in the transportation direction.

The movement of the metering lever within the housing and the triggering of the metering procedure is achieved by pressure loading of a surface of the metering button which is a continuation of the contour of the lid in the rear region of the powder inhaler housing. A circumferential lateral surface, whose contour corresponds to the rounded off end of the powder inhaler housing and which is pushed into the housing through a circumferential slot when the metering button is pressed down, extends downward from the circumference of this surface. Two parallel rockers extend forward through the housing from the two front ends of said lateral surface, in the lower edge region. The distance between the rockers is slightly larger than the width of the powder cartridge so that when it is being inserted the powder cartridge can be pushed through the space between the rockers. The front ends of the rockers are connected to one another by means of a bridge from which bearing journals extend on both sides in bearing holes in the lateral surfaces of the second vertical element of the functional carrier, in which lateral surfaces the metering lever is also pivotably mounted at other points. The bridge has on the front side a step bearing for receiving a restoring spring whose other end is supported in a bearing on the rear side of the vertical plate of the functional carrier. When the metering button is pressed in, the restoring spring is compressed and tensioned. Immediately after the release of pressure, the metering button is pivoted back into its initial position by the restoring spring so that a renewed activation is possible. The means for activating the impulse transmitter and for acting on the metering lever are arranged on the rockers. These means are a driver journal which is arranged on one of the rockers on the outside and has the purpose of acting on an obliquely running stop edge of a lateral surface of the metering lever and a projection which extends upwardly from the other rocker and also projects beyond the rocker toward the inside in order to activate the impulse transmitter. The distance from the driver journal for engaging with the metering lever is smaller than the distance from the projection which acts on the impulse transmitter. By pressing in the metering button, the impulse transmitter is initially activated on the first half of its movement path and as a result the filling of the metering cavity in the metering device is promoted. Further pressing in of the metering button moves the driver journal of the metering button into contact with the stop edge on a lateral surface of the metering lever, and the metering lever is moved on into the center position in which the locking, already described, of the metering lever to the arm of the valve flap occurs, so that in the event of inadvertent release of the pressure on the metering button, the latter returns into its initial position but the metering slide continues to be held in the center position. Renewed activation of the metering button leads to the powder cartridge being supplied with a further energy impulse by the impulse transmitter but does not lead to any pharmaceutical powder being removed from the powder reservoir because the metering slide is not located in the filling position but rather in a center position in which the metering cavity is connected neither to the outlet opening in the funnel nor to the discharge opening in the metering slide duct. Only renewed pressing in of the metering button over more than half of its possible travel releases the locking of the metering lever in the center position and further pressing in of the metering button up to the limit point moves the metering lever into the limit position. At the end of the metering procedure, the metering slide is located in the emptying position and held by the metering lever which has been locked in the limit lock position, so that the powder inhaler is ready for inhalation. This readiness for inhalation is maintained even when the metering button returns to its initial position. Renewed further activation of the metering button only leads to the impulse transmitter being activated but remains without effect on the metering lever which is locked in the limit position so that incorrect dosages before the actual inhalation procedure are ruled out.

During inhalation, by sucking on the mouthpiece, air is sucked by the user through at least one or more openings in the rear part of the inhaler housing into the housing interior and then through the valve chamber into the air duct. A partial air stream is branched off from the air duct through a transverse duct which serves for the transportation of the dose of pharmaceutical powder from the metering cavity of the metering slide through the powder duct into the dispersing device arranged in the mouthpiece. This dispersing device has a chamber which is formed by a baffle plate as front wall, a plate as rear wall and an outer chamber wall arranged between them, the outer diameter of which chamber is smaller than the inner diameter of the mouthpiece surrounding the dispersing device so that an annular space which surrounds the chamber is constructed within the mouthpiece and the outer chamber wall is divided into webs by a plurality of slits extending tangentially into the chamber interior. The outer diameter of the baffle plate is larger than the outer diameter of the chamber so that its edge fits tightly against the inside of the mouthpiece. The baffle plate has in the center an outlet opening from which an outlet duct extends through a truncated cone-shaped connector attached to the front side of the baffle plate. In the edge region of the baffle plate there are a plurality of passage openings distributed symmetrically over the circumference, through which passage openings powder-free air can pass from the annular space into the space in front of the baffle plate. The front end of the powder duct which starts at the rear side of the baffle plate is connected to one of the slits in the outer wall of the chamber and the rear end of the powder duct which extends to underneath the supporting surface of the functional carrier is constructed so as to be capable of being fixed in a vertical element of the functional carrier, which element extends downward from the supporting surface as far as the inner wall of the housing.

A partial air stream conveys the pharmaceutical powder dose through the powder duct into the dispersing device. In order to minimize an undesired, premature transfer of the medicament dose from the metering cavity of the metering slide into the dispersing device before the actual inhalation procedure, the powder duct has a downward curvature in order to form a pocket. During the sucking, the powdered medicament dose is transferred into the chamber interior with the partial air stream through the powder duct and through a tangentially running slit in the outer wall of the chamber. The partial air stream which is necessary for this is branched off from the main air duct and fed through a purging air duct of the metering device. As a result of the fact that the partial air stream which conveys the powder passes through the metering cavity and enters the powder duct, complete emptying of the metering cavity is ensured. The dispersing air stream passes through the air duct into the annular space surrounding the chamber. As a result of the fact that the outer wall of the chamber is divided into a plurality of webs by the slits running into the chamber interior, the dispersing air which is necessary for dispersing the pharmaceutical powder and disintegrating it into fine particles is sucked into the chamber tangentially during inhalation. The surface of each of the webs which faces the chamber interior is constructed as a continuous extension of the slit wall so that the chamber has a polygonal cross section.

The structural design of the dispersing device makes it possible to disintegrate and disperse pharmaceutical powders with different structures.

It is possible to disperse powder formulations in which fine primary particles of an active ingredient are agglomerated (so-called nuclear agglomerates). These agglomerates are disintegrated in the chamber interior by the convergence of the partial air stream which is charged with powder with the dispersing air stream, the fine particles are dispersed in the air and discharged from the chamber with the inhalation air stream.

Another type of powder are so-called adhesive mixtures in which fine particles of active ingredient adhere to carrier particles. Such powder formulations are disintegrated in the chamber, the fine particles of active ingredient becoming detached from the carrier particles, being dispersed in the air stream and discharged from the chamber. The relatively more solid carrier particles remain in the chamber longer and are discharged with a delay with respect to the fine particles of active ingredient during inhalation or are not discharged during inhalation and must be removed from the chamber from time to time during cleaning. The carrier particles which are discharged with delay are for the most part already deposited in the mouth or throat region of the inhaling person.

In order to avoid direct fanning out of the air stream charged with powder and flowing back as a result of a nozzle effect at the end of the outlet duct of the metering device, a partial air stream is branched off through the passage openings arranged in the edge region of the baffle plate from the air stream which is fed to the chamber. This air is directed onto the outer surface of the truncated cone-shaped connector element on the front side of the baffle plate through a radially extending annular web which is arranged at a distance in front of the baffle plate, said air being deflected by the connector element so that a powder-free surrounding air stream which coaxially surrounds the air stream charged with powder emerges from the central opening of the mouthpiece. The fanning out of the air stream which occurs unavoidably as a result of the nozzle effect and the flowing back occurs predominantly from the powder-free surrounding air stream and brings about a very good transfer of the dose of pharmaceutical powder into the mouth and throat region of the inhaling person and from there on into the bronchi of the inhaling person.

The branching off of a further partial air stream from the air stream which is fed to the dispersing device leads to a reduction in the overall resistance of the powder inhaler. As a result of the overall cross section of the openings in the baffle plate of the dispersing device, the overall air resistance of the powder inhaler can be reduced without the dispersal and disintegration of the powder in the chamber being at the same time substantially influenced or modified.

The chamber is an essential part of the dispersing device. It is hollow cylindrical on the outside and has a specially constructed inner wall of the cylinder, into which inner wall the partial air stream which is charged with powder and the additional dispersing air enter through slits which extend tangentially through the outer wall of the chamber of the cylinder. An overall stream with uniformly distributed powder which has disintegrated into fine particles leaves the chamber through the outlet opening in the center of the baffle plate which bounds the chamber on the front side.

The inner wall of the chamber is constructed in such a way that the cross section of the chamber is in the shape of a polygon perpendicularly with respect to the longitudinal axis, an octagon in the case of eight distributed slits and a hexagon in the case of six slits. In principle more than eight slits are also possible. The number can also be less but should not be too small to permit the formation of a cyclone flow. As a result of the fact that the diameter of the outlet opening in the baffle plate is smaller than the inner diameter of the chamber, the risk of coarse particles emerging from the chamber is considerably reduced. The structural design of the inner surface of the chamber reduces the risk of contamination of the inner walls as a result of the adhesion of more highly adhesive primary particles such as occur with a cylindrical chamber wall. As a result of the powder duct whose end is connected to one of the slits, the chamber is not of symmetrical construction. The wall surface of the polygonal inner chamber in which the powder duct opens is unavoidably somewhat larger than that of the other surfaces and the slit which connects the powder duct to the chamber interior is approximately twice as wide as the slits through which the additional dispersing air enters the chamber. The relatively large number of air inlet slits causes an air jacket to be formed between the inner wall of the chamber and the introduced powder and reduces the contact between disintegrated fine particles of powder and the inner wall of the chamber.

The chamber has a double function, its structural design triggers the disintegration of the powder, and almost completely separates out coarse particles from the inhalation stream emerging in the center.

The residence time of soft agglomerates with a given particle size and specific density depends mainly on their tangential speed and thus on the tangential speed of the air entering the chamber tangentially.

The dwell time of the powder in the chamber can be modified not only as a result of the ratio of the partial air streams but can also be varied by changing the distance between the baffle plate and the rear wall of the chamber, and can also be varied within certain limits by means of the diameter of the chamber. The modification of the length of the chamber makes it possible to adapt the dispersing device to the requirements of different powder formulations without the structural design of the functional carrier and the operating elements which are fitted to it having to be fundamentally modified. All that is necessary is to offset the vertical element of the functional carrier (plate), which forms the rear wall of the chamber, in the direction of the longitudinal axis and to increase the length of the webs which are attached to the rear side of the plate forming the rear wall, and which form the outer wall of the chamber.

The compact design of the dispersing device has the advantage that the mouthpiece which is arranged on the front side of the powder inhaler housing is of relatively short construction and makes it possible for the powder inhaler to be of compact design. Furthermore, the premature deposition of fine-particled active ingredient in the powder inhaler, in particular the mouthpiece, is minimized.

The housing of the powder inhaler, the mouthpiece, the dispersing device, the functional carrier, metering button, metering lever, impulse transmitter, drive device for the display device in the powder cartridge and the valve flap can be manufactured from injection moldable plastics. Medically acceptable qualities of polyethylene, polypropylene, poly-carbonate, polyurethanes, polyacrylate, polystyrene, and acrylonitrile butadiene styrene polymers are particularly preferred.

The springs are manufactured from metals or metal alloys which are known and suitable for the purpose.

In contrast, the spring elements of the impulse transmitter and of the counting mechanism drive are likewise made of plastic and are integrally injection molded directly onto the lever of the impulse transmitter or of the functional carrier.

EXAMPLE OF A PREFERRED EMBODIMENT

FIG. 1 shows a vertical section through the pharmaceutical powder cartridge 100 with a central reservoir space 101 for the powdered medicament in a multiple dose quantity. Over a substantial part of its length the cartridge has a cross section in the form of a circle which is flattened on both sides, as is clear in FIG. 3, a horizontal section along the line G–H in FIG. 1. The side wall of the reservoir space 101 has two straight side wall parts 101*a* which lie opposite one another and two curved side wall parts 101*b* which connect said straight side wall parts 101*a*. On one side of the connection points of the straight and curved side wall parts 101*a*, 101*b*, guide ribs 117 which are directed outward in each case are constructed in order to construct an overall cross section of the medicament cartridge 100 which permits insertion into a powder inhaler only in a predetermined position. In the region of the upper edge 102, the reservoir space 101 has a circular cross section and the reservoir space 101 can be closed by means of a lid which can be inserted into the upper edge 102. In the lower region 104, the reservoir space 101 tapers in a funnel shape and ends with an outlet opening 105. The straight parts 101*a* of the side wall of the reservoir space 101 continue linearly as webs 101*c* in the lower region outside the funnel 104*a*, as is clear from the sectional drawings 2 and 3*a*.

In order to be able to supply the lower part of the cartridge 100 with an energy impulse by striking during the triggering of a metering procedure, a web 116 extends outward in the funnel-shaped region 104 from the outside of the funnel 104a in the radial direction of the cartridge to the outer circumference of the cartridge. The arrangement of the web can also be seen in the sectional drawing 3a.

The integrated metering device 107, 123 is arranged on the base of the cartridge 100. Constructed between the lower base surface of the reservoir space 101 and the cartridge base 107 is a duct 108 for a horizontally movable metering slide 123 which, with the cartridge base 107, forms the metering device. The upper side of the metering slide duct 108 is covered on one side of the funnel 104a by a wall 131 which extends from the outside of the funnel 104 at the lower end as far as the outer circumference of the cartridge 100 and about which the legs of the metering slide 123 with a U-shaped cross section engage.

In the cartridge base 107 outside the funnel 104a there is, on one side, a discharge opening 109 which leads down and out and which corresponds to an opening 110 for purging air in the upper wall of the metering slide duct 108. The opening 110 forms the end of an air duct 111 constructed outside the reservoir space 101 in the funnel-shaped region 104. This duct 111 is also represented in the sectional FIG. 3a. In order to construct said duct 111, two webs 111a, 111b, which laterally bound the air duct 111, extend from the outer wall of the funnel 104 parallel to the extended side wall components 10c. The air duct 111 is open on the outside of the cartridge.

The upper edge 102, represented in FIGS. 1 and 2, of the cartridge 100 continues the curved parts 101b of the reservoir space 101 and widens the straight parts 101a to form the circle as is shown in FIG. 2. The upper edge 102 of the reservoir space 101 is surrounded on the outside at a small distance by an annular outer edge 103 which is offset from the side wall of the reservoir space 101. The outer edge 103 is of higher construction than the edge 102 and projects beyond it and has on the inside a small shoulder for receiving the outer wall of a cartridge lid 121. A plastic film strip (not illustrated) which indicates metering units can be inserted into the annular gap 112 which is open at the top between the outer edge 103 and the upper edge 102. The annular gap 112 can then be closed by the lid 121 which is represented in section in FIG. 5 and whose outer edge has a diameter which corresponds to the inner diameter of the outer edge 103, by inserting the lid. The film strip is thus protected against falling out or removal.

The outer edge 103 has at one point a viewing window 113 through which the position of the plastic film strip which is provided with marks can be viewed from the outside. The outside of the outer edge 103 preferably has a profile on at least a part of the circumference in order to make it easier to take hold of and grip the cartridge 100 when inserting it into the powder inhaler.

FIG. 2 shows the cartridge 100 in a longitudinal section along the line N–O in FIG. 1. The distance between the side wall parts 101a of the reservoir space 101 which is smaller in this direction as a result of the departure of the cross section from the circular shape can be seen. In the region of the upper edge 102 of the cartridge 100, the diameter of the interior is increased between the wall parts 101a so that there is a circular cross section of the reservoir space 101. The sections 101a, lying opposite, of the side wall of the reservoir space 101 are offset towards the inside underneath the edge 102. The circumferential outer edge 103 with the annular gap 112 for receiving a film strip is represented in another view. In this sectional view it is shown that the shoulder which connects the outer edge 103 to the side wall 101a of the reservoir space 101 has at one point in the region of a wall part 101a a downwardly directed, offset opening 114 which extends into the annular gap 112, for the engagement of a toothed transportation wheel 74, for the horizontal displacement of an inserted film strip which, for this purpose, has on the lower edge for example a toothing in which the teeth of the toothed transportation wheel 74 can engage.

The funnel-shaped construction of the reservoir space 101 in 104a in the lower cartridge region 104 with the outlet opening 105 can also be seen in this view in FIG. 2. The outlet opening 105 is preferably oval in shape with a longer extent transversely with respect to the longitudinal direction of the metering slide duct 108. This permits larger cavities in the metering slide 123 whose available travel between the filling position and the emptying position is bounded by the outer dimensions of the cartridge as a result of the fact that the metering cavity 124 cannot be opened to any degree with respect to the outlet opening 105 and the discharge opening 109 simultaneously. The metering slide duct 108 has a U-shaped cross section, the legs 115 facing the reservoir space 101. The lower wall of the metering slide duct which connects the legs 115 is also the cartridge base 107.

FIG. 4 shows a section along line J–K in FIG. 1 and makes clear the complex shape of the metering slide duct 108. The outer walls of the two legs 115 of the metering slide duct 108 have recesses 118 which permit positively locking engagement of activation means 71 on the metering slide 123 and permit its horizontal displacement. The height of the metering slide duct 108 can be modified during the manufacture of the cartridge 100 by modifying the distance from the cartridge base 107 in the mold. As a result, the volume of the metering cavity 124 in the metering slide 123 can be modified in addition to the horizontal dimension of the metering cavity 124 and can be adapted to the desired metering quantity.

FIGS. 6a to d show the structural design of the metering slide 123 from above (a), in longitudinal section (b), from below (c) and in cross section (d). An oval metering cavity 124 is constructed transversely with respect to the longitudinal direction in an end region in order to receive the powdered medicament dose from the reservoir space 101 of the cartridge 100, in a position in which the cavity 124 is aligned with the outlet opening 105 of the cartridge 100. A protruding element 125 with a downwardly directed stop 130 for engaging in the slot 119 on the cartridge base 107 is constructed at the opposite end of the metering slide 123. On the upper side of the protruding element 125, a transversely running, wedge-shaped, shallow groove 126 is constructed in which a lug (not illustrated) from the upper wall of the metering slide duct 108 can lock in a sprung manner in order to fix the metering slide 123 when the cartridge is being filled and during transportation. On the two longer outer sides of the metering slide 123 there are recesses 127 for fingers 71 of a metering lever 68 of the powder inhaler 1 to engage in in order to move the metering slide 123. On the underside of the metering slide 123 there is a slight, strip-shaped elevation constructed around the cavity 124 and running from it in the direction of the protruding element 125, with two parallel strips in order to reduce the supporting surface of the metering slide 123 on the base of the metering slide duct 108 and to make the slide 123 easier to move. This raised portion also acts as an additional seal of the cavity 124 with respect to the metering slide duct 108 under the metering slide 123 and reduces the risk of powder entering the metering slide duct 108 from the cavity 124 under the metering slide 123.

In cross section d of FIG. 6, the U-shaped profile of the metering slide 123 is represented, the upwardly directed legs 129 of which metering slide 123 are intended to ensure the precise guidance of the metering slide 123 in the metering slide duct 108. In the cross section d, the downwardly projecting stop 130 can also be seen. The metering slide 123 can be displaced in the metering slide duct 108 between three positions. In the transportation position, the metering slide 123 is inserted as far as possible into the metering slide duct 108 and the lug of the upper duct wall engages in the keyway 126 on the protruding element 125 of the metering slide 123 and holds the metering slide 123 tight in the transportation position. This position is set during the assembly of the cartridge when the metering slide 123 is inserted. In this position, the cavity 124 of the metering slide 123 is approximately flush with the outlet opening 105 of the powder reservoir space 101 for the medicament powder.

In the filling position, the locking securement of the lug in the keyway 126 is released and the metering slide 123 is slightly displaced laterally in the metering slide duct 108 to such an extent that the outlet opening 105 of the powder reservoir space 101 is aligned with the metering cavity 124 of the metering slide 123 in order to receive powder. This filling position of the metering slide 123 is reached for the first time after the cartridge 100 is inserted into a powder inhaler 1.

An emptying position of the metering slide 123 is reached during the activation of the metering procedure by further lateral displacement of the metering slide 123 into a position in which the metering cavity 124 is aligned with the discharge opening 109 in the cartridge base 107 and the purging air opening 110. In this position, the metered quantity of powder can be transferred through the opening 109 into an adjoining powder duct 15 of the inhaler 1.

The three-piece pharmaceutical powder cartridge 100 with the cartridge base 107 and the lid 121 is preferably manufactured from polystyrene and the metering slide 123 which can be inserted into the metering slide duct 108 is preferably manufactured from polypropylene. The dose removal display which is likewise integrated into the cartridge 100 as a result of a particular construction of the upper edge region of the cartridge 100 also includes an additional plastic film strip or injection molded ring with marks, the lower edge of which ring is constructed as a toothing. Such film strips with marks can be readily punched out from plastic films. When the cartridge 100 is assembled, before filling and insertion of the lid 121 the film strip is inserted into the annular gap 112 in such a way that the display indicates 0 removed dose units in the viewing window 113. When a dose is removed, the strip is rotated about the longitudinal axis of the cartridge by a toothed wheel 74 which engages in the opening 114. As soon as the preselected number of doses has been removed from the pharmaceutical powder cartridge 100 and transferred into the powder inhaler 1, the mark which can be seen in the viewing window 113 of the outer edge 103 indicates the imminent complete emptying of the pharmaceutical powder from the cartridge 100 so that, for the sake of the functional capability of the powder inhaler, a powder change in the powder inhaler is requested. Instead of figures, the removal can also be visually indicated by color distinctions.

After the cavity 124 in the metering slide 123 has been emptied through the discharge opening 109 into a powder duct 15 of the powder inhaler 1, the metering slide 123 must be returned into the metering position. The means which are required for this are arranged in the powder inhaler and are parts which are separate from the cartridge.

As a result of the structural design of the metering slide duct 108 with lateral recesses in the legs 115, an activation of the metering slide 123 before insertion into a powder inhaler 1 is made more difficult, especially since the transportation-secured locking of the metering slide 123 to the lug of the upper wall of the metering slide duct 108 must firstly be released. Although this does not require any large application of force, it is only possible by engaging through the recesses in the side walls of the metering slide duct as far as the recesses in the lateral surface of the metering slide so that inappropriate handling of the pharmaceutical powder cartridge is necessary before insertion into a powder inhaler in order to gain access to the contents of the cartridge.

The lid 121 which is fitted in a countersunk manner with a tight fit cannot be removed without destroying it and it also protects the contents against removal or contamination.

FIG. 7 shows a powder inhaler 1 for receiving a medicament cartridge 100 in longitudinal section viewed from above. The powder inhaler housing is composed of two half shells 4 which engage one in the other according to the tongue and groove principle. A so-called functional carrier 50 with horizontal and vertical parts (elements) 12, 50b, 50c, 54, 61 is arranged in the housing formed from the shells 4, which functional carrier 50 divides the interior and is fitted with operating elements. The hollow cylindrical or truncated cone-shaped mouthpiece 3 with dispersing device 2 arranged therein adjoins the housing 4 of the powder inhaler 1 on the front side. The dispersing device 2 has a chamber 8 with a baffle plate 5 as front wall, a plate 12, held by the functional carrier 50 by means of a rib 50c, as rear wall and an annular outer wall which is arranged between the latter and comprises webs 14 and slits 13 which are formed between the webs 14 and run tangentially with respect to the chamber interior. However, with this structural design, the plate 12 of one of the vertical elements of the functional carrier simultaneously forms, as part of the dispersing device 2, the rear wall of the chamber 8. The outer wall of the chamber has a smaller outer diameter than the inner diameter of the mouthpiece 3 so that an annular space 17 surrounding the chamber 8 is constructed within the mouthpiece 3. The outer diameter of the baffle plate 5 is larger than the outer diameter of the chamber 8 to such an extent that the outer edge of the baffle plate 5 fits tightly against the inner wall of the mouthpiece 3. As a result of this structural design of the baffle plate 5, the annular space 17 about the chamber 8 is sealed off from the opening 25 of the mouthpiece 3 and the position of the dispersing device 2 within the mouthpiece 3 is fixed. At the outer edge of the baffle plate 5 there are a plurality of passage openings 18 arranged distributed symmetrically over the circumference in order to branch off out of the annular space 17 a powder-free partial air stream from the dispersing air stream before it enters the chamber 8, which powder-free partial air stream enters the space 11 within the mouthpiece 3 in front of the baffle plate 5 through the openings 18. The baffle plate 5 has in the center an outlet opening 7 for the air stream which is charged with powder and which is fed through an outlet duct 9, constructed by means of a hollow truncated cone-shaped connector element 6 on the front side of the baffle plate 5, to the central opening 25 of the mouthpiece 3. In order to deflect radially to the connector element 6 the partial air stream which enters the annular space 11 through the openings 18 in the baffle plate 5, an annular web 10 extends radially toward the inside at a small distance from the front end of the mouthpiece 3, to such an extent that an annular gap is constructed between the inner edge of the web 10 and the outside of the connector element 6. The hollow truncated cone-shaped connector element 6 is fitted, with its larger base having been rounded off, onto the baffle plate 5 so that the partial air stream which is deflected radially in the annular space 11 by the web strikes the outer surface of the connector element 6 and is deflected to the outlet opening 25 of the mouthpiece. This resulting annular partial air stream surrounds the air stream, charged with powder, from the outlet duct 9 as a surrounding air stream.

The opening on the front side of the housing of the powder inhaler for the mouthpiece to engage in is essentially closed by a plate 54 which extends upward, as a further vertical element of the functional carrier 50, from the horizontal element of the functional carrier 50. In the plate 54 there are passage openings 55 for the dispersing air which passes through them out of the valve chamber 51 through an air duct to the plate 12 and into the annular space 17. A horizontal component of the functional carrier 50 extends from the rib 50c as far as the valve chamber 51 and seals the latter off at the top. The valve chamber 51 is closed from the rear end of the interior of the powder inhaler 1 by means of a valve flap 52. The sucked in air which is necessary for inhaling can enter the interior of the housing through slits in the housing shells 4 and passes through the rear opening 53 after the valve flap 52 has been pivoted into the valve chamber 51. The powder inhaler is ready for inhalation when the locking of the valve flap 52, in the position in which it closes the opening 53, has been released with a metering lever (not shown). The valve flap 52 can then be pivoted into the valve chamber 51 by the sucked in air stream and can clear the opening 53 for air to enter the valve chamber 51. The air can flow out of the valve chamber 51 through the air duct to the dispersing device 2.

The rib 50c of the functional carrier 50 is divided at the end facing away from the baffle plate into two vertical elements 50b which extend upward from the horizontal part.

The horizontal part of the functional carrier 50 has in the center region a shaft 61 (second vertical element of the functional carrier) which extends upward from the supporting surface 56 and has two side walls which are constructed at a distance from one another and whose inner cross section is matched to the outer contour of the powder cartridge to be inserted and which, in addition to the powder cartridge, also has space for receiving operating elements. Two inwardly open guide rails 62 which are located one opposite the other are provided in the side walls of the shaft, into which guide rails 62 guide webs on the outside of the powder cartridge engage when the powder cartridge is inserted, and ensure the correct insertion of the powder cartridge into the powder inhaler. As a result, the insertion of a replacement cartridge which has a different active ingredient, a similar contour and the guide webs in another position with respect to one another is also simultaneously prevented.

Figure 8:
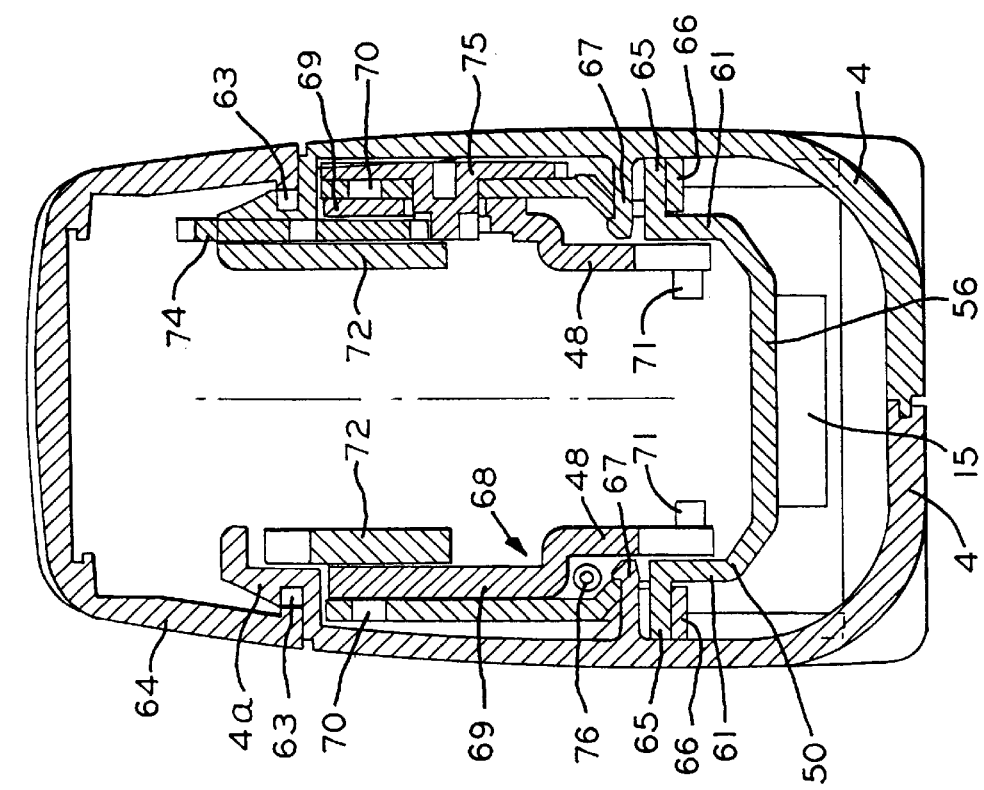
FIG. 8 is a section along line A—A in FIG. 7 and it shows a cross section of the powder inhaler, viewed from the front, without a powder cartridge inserted.

FIG. 8 shows a section along line A—A of FIG. 7 viewed from the front side of the powder inhaler. On the underside of the housing 4, the two half shells 4 are connected by means of a groove/tongue joint which is continuous as far as the rear. In the center region of the powder inhaler, the housing which is formed from the shells 4 is open at the top and can be closed by a lid 64 which can be fitted onto the opening edge from the front and has a U-shaped cross section. The lid 64 engages, with downwardly directed wall parts which run around starting from the edge, the upper part of a powder cartridge (not shown), in particular the part which protrudes from the opening on the upper side of the housing. The lid 64 can be pulled off toward the front in order to insert a powder cartridge. In order to permit this, the edge of the downwardly directed wall parts has webs which are pulled inward and which engage in grooves 63 in the edge 4a of the housing shells when the lid is fitted on. In order to achieve a smooth joint on the outside of the powder inhaler housing between the lid 64 and housing shells 4, the upper edge 4a of the housing shells 4 is offset toward the inside and the grooves 63 are provided in the inwardly offset part.

In FIG. 8, the structural design of the functional carrier 50 and its arrangement inside the powder inhaler housing are represented in greater detail. The side walls of the shaft 61 extend upward from the supporting surface 56 for the powder cartridge. The powder duct 15 which extends to underneath the horizontal supporting surface 56 is represented schematically. Webs 65 which are directed laterally outward extend from the side walls of the shaft 61 as far as the inside of the housing shells 4 which rest on inwardly directed webs 66 of the housing shells 4. In order to hold the housing shells 4 on the functional carrier 50, the housing shells 4 have inwardly directed locking elements 67 above, and at a distance from, the webs 66, which locking elements 67 lock into correspondingly arranged openings in the side walls of the shaft 61. The metering lever 68 for activating the metering device which is integrated into the cartridge which is to be inserted is arranged within the shaft 61. The metering lever 68 has two lateral surfaces 69 which are connected to one another by means of a bridge (not shown). On the outer sides of the lateral surfaces 69 there are bearing journals 70 which are directed outward in the upper region, engage in correspondingly arranged bearing bushes in the side walls of the shaft 61 and permit the metering lever 68 to pivot about the axis of rotation (pivotal center) formed by the bearing points. At the lower ends of the lateral surfaces 69 of the metering lever 68 there are inwardly offset arms 48 with inwardly directed fingers 71 which act in a positively locking fashion on the metering slide in the metering device of the cartridge in order to move said metering slide. The fingers 71 are at a sufficient distance from the pivotal center of the metering lever 68 so that a pivoting movement of the metering lever 68 results in an essentially horizontal movement of the fingers 71 in order to activate the metering slide of the metering device. Two parallel rockers 72 of a metering button 73 extend between the lateral surfaces 69 of the metering lever 68. The toothed transportation wheel 74 of the drive device for the display device in the upper edge of the powder cartridge is represented in the sectional view, said toothed transportation wheel 74 being mounted outside the right hand rocker 72 on a journal on the inside of the recessed edge of the housing shell 4. The toothed transportation wheel 74 engages through the recess on the shoulder of the outer edge of the cartridge in the teeth in the lower edge of the film strip in order to move said film strip in accordance with the removal of doses from the cartridge. The toothed transportation wheel 74 is engaged with a toothed pinion 75 (transmission wheel) which projects through an opening 45 in the side wall 69 of the metering lever 68 and has on the outside a toothed disk with a larger outer diameter than that of the toothed ring for engaging with the toothed transportation wheel 74. There is space, in addition to the arms 48, offset from the lateral surfaces 69, of the metering lever 68, for a restoring spring 76 which pulls the metering lever 68 toward the rear into the initial position after locked connections have been released.

FIG. 9 is a section along the line B—B of FIG. 7 viewed in the same way as FIG. 8. In the rear part of the powder inhaler a part 73a with U-shaped cross section of the metering button 73 projects beyond the downwardly offset upper housing wall. For their connection, the housing shells 4 have surface parts which are directed inward toward one another and have a catch connection so that the shells 4 are held together and the housing is sealed at the top. The downwardly directed, circumferential side wall of the metering button 73 is pushed, when activation by means of pressure takes place, into the housing through a slit with a corresponding contour. Two parallel rockers 72 extend, at a distance from one another, inside the housing from part 73*a* of the metering button through the space between the metering lever 68 and the powder cartridge and permit the metering button 73 to be coupled to the lateral surfaces of the second vertical element of the functional carrier 50 by means of bearing journal 92*a*. The metering lever 68, with its lateral surfaces 69, which surrounds the rockers 72 of the metering button 73 on the outside extends into this region outside the shaft 61 for the powder cartridge.

In this region, the functional carrier 50 has arms 50*a* which extend upward from the horizontal part and have bearing bushings at the upper ends. A so-called impulse transmitter 78 with a hammer 79 which faces the cartridge 100 has at its upper end a shaft 80 with two outwardly directed bearing journals which engage in bearing bushes in the arms 50*a*. At the impulse transmitter 78 there is, at a distance, a laterally offset transverse spring element 81 with a projection 82 which has an outwardly directed oblique surface 82*a*. The oblique surface 82*a* interacts with a projection on a rocker 72 of the metering button 73 so that, when the metering button 73 returns into the initial position, said oblique surface 82*a* can move its projection laterally past the transverse spring element.

An angled movable plunger 47 is inserted into a gap 77 of the functional carrier 50 above the valve chamber 51, extends into the cartridge shaft and, when the cartridge is inserted, said plunger acts temporarily on the valve flap 52 in order to release its possibly still existing locked connection to the metering lever 68. In this way it is ensured that the metering lever 68 is pulled into its initial position by its restoring spring when a new cartridge is inserted.

Elements of the functional carrier which extend downward from the horizontal part of the functional carrier 50 as far as the base function as side walls of the valve chamber 51. The latter has an opening 53 which is closed off from the rear part of the housing with a valve flap 52 which is coupled to functional carrier elements.

FIG. 10 shows a vertical longitudinal section through the powder inhaler viewed from the side, for the sake of better comprehension of the insertable powder cartridge only the metering slide 123 of the metering device which is integrated into the cartridge is schematically represented in the filling position, in order to illustrate the interaction with the fingers 71 on the arms 48 of the metering lever 68.

On the front side of the housing 4, the mouthpiece 3 with dispersing device arranged thereon is inserted into the housing. During sucking in for inhalation, the air stream charged with powder emerges through the central outlet opening 25 in the mouthpiece 3. The truncated cone-shaped connector element 6, which surrounds the outlet duct 9, extends forward from the baffle plate 5. In front of the baffle plate 5 there is an annular space 11 which is bounded with respect to the central opening 25 of the mouthpiece 3 by a radial web 10. A surrounding air stream which is free of powder and which surrounds the air stream which is charged with powder and which emerges from the duct 9 is formed in the annular space 11 by deflecting the partial air stream which enters through the openings 18 in the baffle plate 5. The interior 8 of the chamber is sealed off at the rear by the plate 12 which extends upward from the functional carrier 50.

The wall of the powder duct 15 extends on the underside of the rear of the baffle plate 5 to underneath the supporting surface 56 on the functional carrier 50 for the powder cartridge. The upper side of the powder duct 15 is closed by a horizontal part of the functional carrier 50. The powder duct 15 has a downwardly curved section in order to form a pocket 30 within the powder duct 15 in order to avoid premature transportation of the powder under the force of gravity when the inhaler is held at an angle, said powder passing through the passage opening 57 in the supporting surface 56 into the powder duct 15. A downwardly directed web 60 of the functional carrier 50 can receive, in a recess, a finger at the end of the wall of the powder duct 15 and, in this way, said web 60 fixes the baffle plate 5 and the powder duct 15 to the functional carrier 50. For manufacturing reasons, a component 31 of the housing shell 4 is attached to the wall of the powder duct 15 via a web in order to provide additional securing of the powder duct 15 in its position. At the same time, cleaning of this region of the powder inhaler which may be necessary is in this way made easier after the mouthpiece 3 and the baffle plate 5 with connected powder duct 15 have been removed. At a distance from the rear wall 12 of the chamber 8, a plate 54 extends upward from the functional carrier 50, said plate 54 sealing off part of the housing opening on the front side of the powder inhaler but being at such a distance from the inner wall of the mouthpiece 3 that a partial air stream can pass into the space 17 surrounding the chamber. On the rear side of the plate 54, there is, in the vicinity of the upper end, a bearing 84 for a restoring spring 38 whose other end is mounted in a spring block 86 on the bridge 85 which extends between the front ends of the rockers 72 of the metering button 73. The transverse duct 58 for branching off a partial air stream is arranged at the functional carrier 50 underneath the spring seating pan 86, a web which is directed upward from the duct wall forming a stop for the bridge 85, which stop bounds the movement of the metering button 73 about the pivotal center 92 under the force of the restoring spring.

A lid 64 which can be fitted on engages around the upper edge 4*a* of the housing. In the lid 64 there is, on the end side, a window 87 which corresponds to the viewing window in the outer edge of the powder cartridge and permits the medicament doses which have been removed to be read off. There may be a leaf spring 90 in the lid 64, which leaf spring 90 presses the cartridge against its supporting surface 56. The sectional drawing shows the design of the upper part 73*a* of the metering button 73, which upper part 73*a* extends outside the housing, with the wall part which is directed downward from the activation surface of the metering button 73 and is pushed into the housing when the metering button 73 is activated.

The arrangement of the impulse transmitter 78 with lever 78*a* and with the hammer 79 which is directed toward the cartridge can be seen in this illustration. The impulse transmitter 78 can pivot about the shaft 80 which is mounted with journals in bushes of the arms 50*a* of the functional carrier 50. The transverse spring element 81 extends laterally offset, approximately in parallel, from the elongated lever 78*a* of the impulse transmitter 78 and cannot move in the direction of movement of the impulse transmitter but can move transversely with respect thereto. A drive spring 80*a* is integrally molded on behind the lever 78*a* of the impulse transmitter.

The impulse transmitter 78 is initially moved away from the cartridge, by the driver on the projection (not shown) of the metering button 73 in order to tension it by acting on the surface 35 of a projection on the transverse spring element 81, to such an extent that the upper end of the drive spring 80a is pressed against the inner wall of the housing shell. As the metering button 73 is pressed in further in the region of the first part of its travel, the driver of the metering button slips off the surface 35 so that the impulse transmitter 78 is impacted against the cartridge by the drive spring 81a. In order to have sufficient mass for a mechanical impulse, the impulse transmitter 78 is reinforced in the lower part.

On the side walls of the metering lever 68 there is a lug 91 for hooking in a restoring spring 76. The rockers 72 of the metering button 73 are connected at their front ends to the bridge 85. On the outside of the bridge 85 there are bearing journals which engage in bearing holes of the lateral surfaces of the second vertical element of the functional carrier 50 and form the pivotal center 92 of the metering button 73. The bearing journals 70 in the side walls of the metering lever 68 constitute the pivotal center of the metering lever. They are only indicated in FIG. 10. At the rear end of the metering lever 68 there is a limit lock 93 indicated. At the front end of the metering lever 68 there is an indicating symbol 88 which, when the metering lever 68 pivots, is moved into the region of a window 89 in the housing shell of the end side and indicates the readiness for inhalation after metering has taken place by activating the metering button 73. The stop edge 94 on one lateral surface 69 of the metering lever 68 for the driver 99a on the metering button 73 is indicated schematically on its upper edge.

At the rear end of the functional carrier 50 the valve chamber 51 is constructed from further elements of the functional carrier 50 underneath its horizontal part, said valve chamber 51 having the opening 53 toward the housing interior, which air can enter through slits (not shown) in the lateral surfaces of the housing shells 4 or other openings in the housing.

Figure 11:
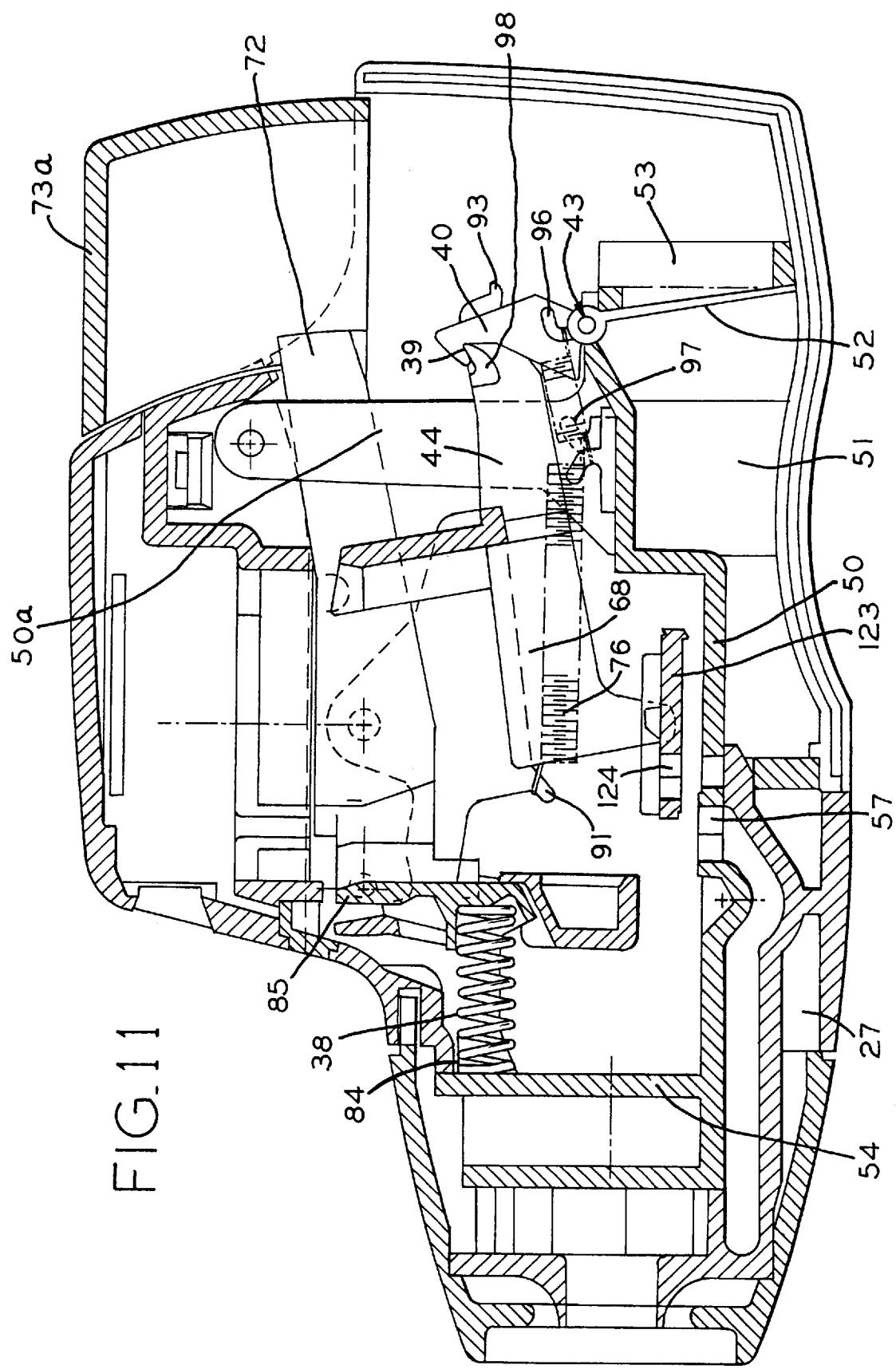
FIG. 11 is a vertical longitudinal section through the powder inhaler, in which figure the metering slide is located in the center position, showing details of the locking of the metering lever with elements of the valve flap.

FIG. 11 is a longitudinal section which is comparable with FIG. 10 and in which the impulse transmitter is not represented but rather the metering button 73/73a with parallel rockers 72 which are connected to the front end by the bridge 85. The interaction of the metering lever 68 with locking elements of the valve flap 52 is likewise shown.

The metering lever 68 is located in a center locking position from which it can be moved on by the metering button 73 only into the limit locking position in which the metering cavity 124 of the metering slide 123 is aligned with the passage opening 57 in the functional carrier 50. In this illustration, the pressure spring 38 between the bearing 84 and the spring block 86 is represented, which pressure spring 38 presses back the metering button 73 into the initial position after it is relieved of load, by acting on the bridge 85. The rockers 72 of the metering button constitute the connection to the part 73a of the metering button 73 outside the housing. As a result of the pressing down of part 73a the metering button rotates about the bearing point 92.

In FIG. 11, the restoring spring 76 which is attached to the lug 91 of the metering lever 68 and has the purpose of returning the metering lever 68 is represented, as a result of which the metering slide 123 in the metering device is simultaneously reset from the emptying position into the filling position of the metering cavity. The valve flap 52 for closing the opening 53 of the valve chamber 51 has an upwardly directed hook 96 for a spring 97 to act on, the other end of which spring 97 is fixed to the functional carrier 50. This tension spring holds the valve flap 52 tight with such a force that in order to suck in air for inhalation it must be overcome so that the valve flap clears the opening of the valve chamber.

In this position of the metering button 73 the latch 98 on the metering lever arm 44 is engaged with the blocking edge of the hook 39 at the upper end of the arm 40 which extends upward from the shaft 43 of the valve flap 52, so that movement of the valve flap 52 by sucking in air is blocked. In this position, resetting of the metering lever 68 into the initial position is likewise blocked. The metering lever 68 can only be moved out of this center locking position and into the emptying position of the metering device by the metering button 73 being pressed in further and acting on the metering lever 68. During this process, the metering button 73 passes back through the second part of its possible travel. In this context, the engagement with the blocking edge on the hook 39 of the arm 40 of the valve flap 52 is released and, instead, the metering lever latches in with its lug 93 in the recess 42 or valve flap shaft 43. Since the geometric conditions of this latch arrangement are completely different, the sucking in of air for inhalation is sufficient to rotate the valve flap and thus release the metering lever again.

FIGS. 12a and b show the design of the metering button 73 in greater detail, FIG. 12a being a side view and FIG. 12b being a plan view. The component 73a for activating the metering button 73 extends above the housing of the powder inhaler. Two parallel rockers 72 start from it and run within the housing, the front ends being connected to one another by a bridge 85. Bearing journals 92a, which engage in correspondingly arranged bushes in the third vertical elements 50b of the functional carrier 50 and form the pivotal center 92 of the metering button 73, extend from the bridge 85 on both sides. On the end side of the bridge 85, the spring block 86 is arranged as a bearing for the restoring spring of the metering button 73. After it is relieved of the activation pressure, the restoring spring immediately presses the metering button 73 back into the initial position without this having to affect the position of the metering lever. If the metering button 73 was only pressed in to such an extent that the impulse transmitter 78 has indeed been tensioned by the driver on the projection 99b and has been relieved of tension again by striking the powder cartridge, the metering button 73 returns into the initial position without having acted on the metering lever 68 so that the latter remains unchanged in the initial position.

If the metering button 73 is moved approximately half its possible travel by pressing in, the driver journal 99a which is provided on the outside of one or more rockers 72 acts on the stop edge or edges 94 of the metering lever 68 and the metering lever 68 is moved into a center position. A projection 99b for tensioning and triggering the impulse transmitter 78 extends upward from the other rocker 72 and projects inward beyond the rocker. For this purpose, the driver engages on the projection 99b on an working surface 35 on a projection on the transverse spring element 81 of the impulse transmitter 78 and pivots the impulse transmitter 78 away from the powder cartridge. As a result of the rotational movement, the upper end of a drive spring 80a, which is injection molded onto the impulse transmitter 78, is pressed onto the inside of the housing shell as a counterbearing and tensioned. The different bearing points of the impulse transmitter 78 and metering button 73 on the functional carrier element 50 also permit the projection 99b to slip off the working surface 35 of the transverse spring element 81 during the movement of the metering button 73 over the first half of its possible travel, so that said projection 99b impacts against the powder cartridge under the effect of the spring force of the drive spring 80a. Said mechanical impulse is intended to promote the correct filling of the metering cavity in the metering slide of the metering device integrated into the powder cartridge. In order to permit the metering button 73 to return into the initial position and to move past the transverse spring element 81 into the basic position when the metering button 73 is returned, the transverse spring element 81 can be deflected transversely with respect to the direction of rotation of the impulse transmitter. Here, an oblique surface which is constructed on a projection 82 which protrudes from the outer surface of the transverse spring element 81 slides over the oblique surface 83 of the projection 99b of the metering button 73.

The metering button 73 acts not only on the impulse transmitter but also, via the driver journal 99a, on the metering lever 68 which is represented in detail in FIGS. 13a to c. This metering lever 68 engages with its lateral surfaces 69 around the powder cartridge.

FIG. 13a is a plan view, 13b and 13c are side views. The two lateral surfaces 69 are connected to one another on the front side of the metering lever 68 by a bridge 49a, which forms the foot of an indicating symbol 88, and at the rear side by means of a bridge 49. As a result of rotation of the metering lever 68, the indicating symbol 88 is moved into the viewing window 89 of the housing shell when the unlocking position is reached, and it indicates readiness for inhalation.

Bearing journals 70 extend from the outer sides of the lateral surfaces 69 and engage in bearing bushes in the lateral surfaces of the shaft 61 of the functional carrier so that the metering lever 68 is pivotably mounted in lateral surfaces, located opposite one another, of the powder cartridge shaft 61 of the functional carrier. Extending from the lateral surfaces 69 are arms 48 which are offset laterally toward the inside and at whose ends there are inwardly directed fingers 71 for engaging in the metering device of the powder cartridge. The pivoting movement of the metering lever 68 about the bearing journals 70 leads to an essentially horizontal movement of the fingers 71 which as a result move the metering slide horizontally. Extending upward from one of the lateral surfaces 69 is a spring arm 46 which, when the metering lever 68 moves, acts on and rotates the drive pinion of the counting device for removed medicament doses. This drive pinion is mounted in a hole 45 in a lateral surface 69 as a bearing bush. The rotational movement of the metering lever 68 as a result of the driver journal 99b of the metering button 73 takes place counter to the spring force of a tension spring which is hooked into the lug 71. An arm 44 for engaging with locking elements of the valve flap extends rearward from the bridge 49, underneath the bridge 49. A hook-shaped latch 98, which serves as first locking element, is laterally attached to the arm 44. At the end of the arm 44 there is a catch hook 93 as a second locking element. The spring which engages on the lug 91 holds the metering lever 68 until the driver 99a of the metering button 73 engages in the initial position, the fingers 71 having moved the metering slide into the filling position of the metering cavity, as shown schematically in FIG. 10.

The metering lever 68 can be rotated out of this position by the driver 99a of the metering button 73 into a first locking position (center position), the metering slide being pushed into a center position between filling and emptying of the metering cavity as a result of the movement of the arms 48 and of the fingers 71. The metering button 73 which can rotate through an angle of 20° has passed through approximately half the possible travel here. A return movement of the metering lever 68 out of this position into the initial position is blocked as a result of the locking of the latch 98 into the blocking edge of the hook 39 on the upwardly directed arm 40 of the valve flap 52, as is indicated schematically in FIG. 11.

The force of the air stream which is exerted on the valve flap 52 as a result of sucking is not sufficient to release this locking engagement because the radii of the latch 98 and the blocking edge on the hook 39 of the valve flap arm 40 are different. This locking position simultaneously also blocks the movement capability of the valve flap 52. As the metering lever 68 moves on as a result of further pressing in of the metering button 73, the locking connection of the latch 98 to the blocking edge on the hook 39 of the valve flap arm 40 is released. When the limit position of the metering lever 68 is reached, that is the position in which the fingers 71 on the downwardly directed arms 48 of the metering lever 68 have moved the metering slide out of the center position into the emptying position, locking of the metering lever 68 is necessary until the inhalation phase in order to counteract the restoring force of the spring which engages on the lug 91 of the metering lever 68. For this purpose, there is a recess 42 on the shaft 43 of the valve flap 52, in which recess 42 the catch hook 93 at the end of the metering lever arm 44 engages and is held by a blocking edge until the valve flap 52 has been pivoted a sufficient distance by the air stream during inhalation. As a result of the delayed release of the locking connection between the metering lever 68 and the shaft 43 of the valve flap 52, it is ensured that the metering cavity is sucked empty in the first phase of the inhalation. After release, the metering lever 68 can be pulled back into the initial position by the springs and said metering lever 68 simultaneously moves the metering slide back into the filling position.

FIGS. 14a to c show the details of the structural design of the valve flap 52 in plan view and sections, said valve flap 52 being mounted by means of a shaft 43 with journals which engage in bushes in the elements of the functional carrier which form the valve chamber. For static balancing, the valve flap 52 with shaft 43 and the upwardly directed arm 40 also has a weight element 41 which extends upward parallel to the arm 40. On this element 41 there is a journal which faces the arm 40 and on which a pinion which engages in a gap of the functional carrier is fitted. When the cartridge is inserted into the powder inhaler the pinion is displaced by the cartridge. This movement is transmitted to the valve flap 52 so that the latter is briefly pivoted in order to release the locking connections of the metering lever 68 to the locking elements of the valve flap 52 and to ensure that the metering lever is moved into its initial position by the restoring springs irrespective of its position before the insertion of the cartridge.

The arm 40 has at the end a hook 39 of a blocking inner edge on which the latch 98 of the metering lever arm 44 can engage in order to produce between the metering lever 68 and the valve flap 52 a locking connection which cannot be released by sucking air through the powder inhaler but rather can only be released mechanically by moving on the metering lever 68. The spring with which the valve flap 52 is pulled back into the vertical position after the inhalation engages on the hook 96 which is seated on the shaft 43. The other spring end is secured to the functional carrier. Further movement of the metering lever 68 releases the locking connection of the latch 98 in the hook 39 at the end of the arm 40 and leads, in the limit position of the metering lever, to the locking engagement of the catch hook 93 of the metering lever 68 into a recess 42 with a blocking edge in the shaft 43 with the arm 40. In this position of the metering lever, the device is ready for inhalation. The engagement of the metering lever 68 with its catch hook 93 in the recess 42 is released by moving the valve flap 52 by means of the air stream with little delay so that the metering lever is pulled back into its initial position by the restoring springs.

FIGS. 15 and 16 show further details of the dispersing device for the medicament powder, said device being arranged in the mouthpiece of the powder inhaler.

FIG. 15 is a longitudinal section in a plane perpendicular to the longitudinal axis of the powder inhaler. With this structural design, the baffle plates 5 with the webs 14, 14a which form the annular outer wall, interrupted by slits 13, 13a, about the chamber 8, and the powder duct 15 are constructed in one piece. The truncated-cone-shaped connector element 6 extends forward from the baffle plate 5. Arranged in the center of the baffle plate 5 is the outlet opening 7 of the chamber 8 from which an outlet duct 9 for the air stream which is charged with powder extends through the truncated-cone-shaped protruding element (connector element) 6. The base of the truncated cone adjoins, in a rounded manner, the front side of the baffle plate 5 in order to deflect the radial air stream which is free of powder, in the longitudinal direction of the duct 9 to the mouthpiece opening.

The rear wall of the chamber 8 is not represented in this figure; said wall is integrated into the functional carrier. The annular outer wall, formed from webs 14, 14*a*, of the chamber 8 has a smaller outer diameter than the baffle plate 5 so that an annular space 17 is constructed between the inner wall of the mouthpiece (not shown) and the outer wall of the chamber 8. Air can enter the interior of the chamber 8 from said annular space 17 through a plurality of slits 13 which extend tangentially as far as the chamber interior. The web 14*a* in the lower wall region divides off the chamber interior from the end of the powder duct 15 and thus gives rise to an asymmetrical design of the chamber 8. A partial air stream can pass out of the annular space 17 into the space in front of the baffle plate 5 through passage openings (not shown) arranged symmetrically in the edge region of the baffle plate 5.

The outer wall 16, with a U-shaped cross section, of the powder duct 15 extends from the rear side of the baffle plate 5 underneath the horizontal part (not shown) of the functional carrier which covers the upper side of the U-profile of the outer wall 16 of the duct. A finger for engaging in a recess in a vertical element of the functional carrier in order to secure said part of the dispersing device to the functional carrier is constructed at the rear end of the outer wall 16 of the duct. The powder duct 15 has a recessed subsection 30. This pocket prevents undesired premature conveying of powder into the dispersing device before the actual inhalation. In order to fix this subelement of the dispersing device better in the powder inhaler, a part of the housing wall is also constructed in the form of an outer contour 31 in the region of the recessed portion 30 by means of a web.

In order to make the asymmetrical construction of the chamber 8 clearer, FIG. 16 shows a plan view of the baffle plate from the rear side, i.e. from the chamber interior. In the center there is the outlet opening 7 of the chamber 8 with which the outlet duct 9, represented in FIG. 15, starts. This plan view clearly shows the construction and arrangement of the webs 14, 14*a* which form the outer wall of the chamber, with the tangential slits 13, 13*a* extending between said webs 14, 14*a*. The end of the powder duct 15 is connected to the chamber interior via the slit 13*a* through which the powder which is to be dispersed and to be disintegrated can pass into the chamber 8. Further air for swirling and disintegrating and dispersing the powder is supplied through the tangential slits 13 by means of the cyclone which is produced. The cross section of the slit 13*a* for the powder to enter the chamber interior from the powder duct 15 is approximately twice as large as the cross section of the slits 13 for the entry of air. In order to achieve a particularly good disintegrating and dispersing effect, the surface 26, facing the chamber interior 8, of the webs 14, 14*a* is constructed as a direct extension of the slit wall and gives rise to a polygonal cross section of the chamber. The number of corners depends on the number of slits. In the figure, seven slits 13 are represented for the entry of air and there is an eighth slit 13*a* for the entry of the partial air stream with powder. The outer wall 16 of the powder duct 15 is of somewhat thicker construction in the further course of the powder duct. The thinner construction of the wall in the region which directly adjoins the baffle plate 5 serves to form, in this region also, the annular space 17 which surrounds the outer wall of the chamber. In order to branch off a partial air stream from the air stream which enters the chamber interior 8 through the slits 13, 13*a*, the baffle plate 5 has in this embodiment six recesses 18 which are offset at the outer edge at an angle of 60° and which form passage openings for air to pass from the annular space 17 behind the baffle plate 5 into the space in front of the baffle plate 5. The number of openings and their arrangement are to be selected such that, overall, there is a cross section which separates off only one partial air stream from the dispersing air stream.

The entire air sucked into the powder inhaler during inhalation is initially broken up within the powder inhaler into two substreams, one of which conveys the powder out of the metering cavity of the metering slide through the powder duct 15 into the chamber interior 8. The second substream passes out of the powder inhaler into the annular space 17 which surrounds the chamber 8, and is divided into a partial air stream, which forms a surrounding air stream, and the dispersing substream, which promotes the dispersal of the medicament powder in the chamber 8. Said partial air stream which serves for dispersal enters the chamber interior through the slits 13 and is reunited in the chamber 8 with the partial air stream conveying the powder, the powder which is fed in being disintegrated in the chamber by a cyclone effect and dispersed in fine particles into the air.

The U-shaped profile of the outer wall 16 of the powder duct 15 is also represented in FIG. 16, with the part 31 of the housing of the powder inhaler, which part is connected via a web to the wall 16 of the powder duct 15.

LIST OF REFERENCE NUMERALS

1 Powder inhaler
2 Dispersing device
3 Mouthpiece
4 Housing of the powder inhaler
4*a* Upper edge at opening on upper side of housing
5 Baffle plate
6 Truncated cone-shaped connector element
7 Outlet opening
8 Chamber
9 Outlet duct
10 Annular web in the mouthpiece
11 Annular space in front of the baffle plate
12 Rear wall of chamber, plate
13, 13*a* Slits running tangentially through the outer wall of the chamber
14, 14*a* Webs of the outer wall of the chamber
15 Powder duct
16 Outer wall of the powder duct
17 Annular space surrounding chamber
18 Passage openings in the baffle plate
25 Central opening in the mouthpiece
26 Inner surface of the webs of the outer wall of the chamber
27 Air inlet duct 28 Baffle surface of the powder duct
29
30 Pocket in the powder duct
31 Component of the housing shell
32
33
34
35 Working surface on the impulse transmitter
36
37
38 Restoring spring of the metering button
39 Hook on the valve flap arm
40 Upwardly directed arm of the valve flap
41 Weight element
42 Recess in the valve flap shaft
43 Shaft of the valve flap
44 Arm on the metering lever
45 Hole in the side wall of the metering lever
46 Spring element arm
47 Plunger
48 Downwardly directed arms of the metering lever
49, 49a Bridges for connecting the lateral surfaces of the metering lever
50 Functional carrier
50a First vertical elements of the functional carrier (arms)
50b
50c Vertical element, ribs on the functional carrier
51 Valve chamber
52 Valve flap
53 Opening of the valve chamber
54 Plate on the functional carrier (vertical element of the functional carrier)
55 Air passage openings
56 Supporting surface for powder cartridge on the functional carrier
57 Passage opening in the functional carrier
58 Transverse duct
59 Opening in the transverse duct
60 Web, vertical functional carrier element
61 Second vertical functional carrier element, shaft for powder cartridge with parallel surfaces (side walls) at a distance from one another
62 Guide rails
63 Grooves on the outside of the housing
64 Lid of the powder inhaler
65 Webs on the functional carrier
66 Webs on the inside of the housing shells
67 Locking elements
68 Metering lever
69 Lateral surfaces of the metering lever
70 Bearing journal of the metering lever
71 Fingers for activating the metering lever
72 Rockers of the metering button
73 Metering button
74 Toothed transportation wheel
75 Toothed pinion, transmission wheel
76 Restoring spring for metering lever
77 Gap in functional carrier
78 Impulse transmitter
78a Lever of the impulse transmitter
79 Hammer, hammer element
80 Shaft of the impulse transmitter
80a Molded on (drive) spring of the impulse transmitter
81 Transverse spring element
82 Projection on the transverse spring element
82a Oblique surface on the projection of the transverse spring element
83 Oblique surface on the metering button
84 Bearing for restoring spring of the metering button
85 Bridge
86 Spring block
87 Viewing window
88 Indicating symbol on the metering lever
89 Window
90 Leaf spring for clamping the lid
91 Lug, hook
92 Pivotal center of the metering button
92a Bearing journal of the metering button
93 Catch hook of the metering lever arm
94 Stop edge on lateral surface of the metering lever
95
96 Hook on the shaft of the valve flap
97 Spring
98 Hook-shaped latch on the metering lever arm
99a Driver on the metering button for the metering lever
99b Projection on the metering button
100 Pharmaceutical powder cartridge
101 Reservoir space for powder
101a Straight parts of the side wall of the cartridge
101b Curved parts of the side wall of the cartridge
101c Lower web-shaped parts of the side wall 101a
102 Upper edge of the cartridge
103 Upper outer edge of the cartridge
104 Lower region of the cartridge
104a Funnel
105 Outlet opening
107 Cartridge base
108 Metering slide duct
109 Discharge opening
110 Purging air opening
111 Purging air duct
112 Annular gap
113 Viewing window
114 Engagement opening
115 Leg of the metering slide duct
116 Web-shaped wall
117 Guide ribs
118 Recesses in the side walls of the metering slide duct
119 Slit in the cartridge base
120 Lug
121 Cartridge lid
122 Connector element
123 Metering slide
124 Metering cavity
125 Protruding element
126 Keyway
127 Recesses
128 Elevation
129 Leg of the metering slide
130 Stop
131 Upper wall of the metering slide duct

We claim:

1. A replaceable pharmaceutical powder cartridge for powder inhalers for holding a supply of medicament for a large number of doses of pharmaceutical powder, said replaceable cartridge including an integrated metering device which comprises at least one metering cavity for holding a predetermined quantity of a pharmaceutical powder, said integrated metering device comprising a metering slide which is movable from a filling position wherein medicament is transferred from said supply into said metering cavity into an emptying position wherein said medicament in said metering cavity is available to a user of the inhaler by substantially transverse movement of said metering slide with respect to the flow direction of pharmaceutical powder into said metering cavity.

2. The pharmaceutical powder cartridge as claimed in claim 1, wherein the metering slide can also be moved into a transportation position.

3. The pharmaceutical powder cartridge as claimed in claim 2, wherein the metering slide is fixed in the transportation position by spring-elastic means.

4. The pharmaceutical powder cartridge as claimed in claim 1, which comprises a lid which can be inserted into an upper edge and has the purpose of closing a reservoir space for a large number of doses of pharmaceutical powder, a side wall of the reservoir space tapering in the lower region of the pharmaceutical powder cartridge in a funnel shape to an outlet opening in the lower region of the pharmaceutical powder cartridge, a device for holding the metering device at the lower end of the pharmaceutical powder cartridge, and a means for feeding in purging air, which means is arranged laterally on the outside of the reservoir space and has the purpose of promoting a complete emptying of the metering cavity of the metering device in its emptying position.

5. The pharmaceutical powder cartridge as claimed in claim 4, wherein the device for holding the metering device is a metering slide duct which is arranged under the lower end of the reservoir space and in which the metering slide is displaceably arranged as a metering device so that in the filling position of the metering slide the metering cavity is located in the region of the outlet opening and in the emptying position of the metering slide the metering cavity is located in the region of the means for feeding in purging air in order to promote complete emptying of the metering cavity, and in the region of a discharge opening which corresponds to the means for feeding in purging air.

6. The pharmaceutical powder cartridge as claimed in claim 5, wherein the metering slide duct is laterally open over a substantial part of its length transversely with respect to the direction of movement of the metering slide so that an activation device can laterally take hold of the metering slide and displace it.

7. The pharmaceutical powder cartridge as claimed in claim 4, wherein, in the transportation position of the metering slide, the metering cavity of the metering slide is located outside the regions of the outlet opening and of the means for feeding in purging air.

8. The pharmaceutical powder cartridge as claimed in claim 1, wherein the metering slide has a U-shaped cross section and there are recesses on the outside of the legs for activation means to engage through the recesses in the side walls of the metering slide duct, and the metering slide has at the end facing away from the metering cavity a protruding element with a downwardly directed stop for engaging in a corresponding slit which extends in the longitudinal direction of the base of the cartridge, as well as a keyway for a lug which faces the metering slide duct to engage in the upper wall of the metering slide duct.

9. The pharmaceutical powder cartridge as claimed in claim 1, wherein the outer edge is constructed to be higher than the upper edge of the pharmaceutical powder cartridge, and the pharmaceutical powder cartridge has a lid with a connector element which, after the insertion of the lid, is held by form fit of the edge of the pharmaceutical powder cartridge, and wherein the outer edge of the lid which extends outward from the connector element extends via the upper edge and the annular gap into a shoulder on the inside of the outer edge and is arranged countersunk within the outer edge of the cartridge.

10. The pharmaceutical powder cartridge as claimed in claim 1, wherein the cartridge lid, the metering slide and the pharmaceutical cartridge are manufactured with the integrated metering device from thermoplastic as separate parts without the metering slide.

11. The pharmaceutical powder cartridge as claimed in claim 1, wherein the pharmaceutical cartridge has on its underside a viewing window by means of which the position of the metering slide can be checked.

12. The pharmaceutical powder cartridge as claimed in claim 1, characterized by a display device for the quantity of medicament doses which have been removed or which remain in the pharmaceutical powder cartridge, the display device for the quantity of medicament doses which have been removed or which remain being integrated into the upper edge region of the pharmaceutical powder cartridge.

13. The pharmaceutical powder cartridge as claimed in claim 12, wherein the display device is formed by a film strip or ring which can be moved along the circumference of the upper edge region of the pharmaceutical powder cartridge.

14. The pharmaceutical powder cartridge as claimed in claim 13, wherein the film strip or ring is provided with a toothing by means of which the film strip or ring can be moved along the circumference of the upper edge region of the pharmaceutical powder cartridge.

15. The pharmaceutical powder cartridge as claimed in claim 13, wherein the pharmaceutical powder cartridge has in its upper edge region an annular gap for receiving the film strip or ring.

16. The pharmaceutical powder cartridge as claimed in claim 15, wherein an outer edge which radially bounds the annular gap on the outside has at at least one point on its circumference a recess in the form of a viewing window so that the film strip or the ring can be seen from the outside.

17. The pharmaceutical powder cartridge as claimed in claim 15, wherein the annular gap is downwardly open at at least one point on its circumference so that a drive wheel for the film strip or ring can project into the annular gap from underneath.

18. The pharmaceutical powder cartridge as claimed in claim 12, wherein the display device is provided with a scale for the quantity of medicament doses which have been removed or remain in the pharmaceutical powder cartridge.

19. An inhaler for powdered medicaments, in which the medicament can be received by a patient by means of an air stream, which inhaler comprises a receptacle for a replaceable pharmaceutical powder cartridge as claimed in claim 1.

20. The inhaler for powdered medicaments as claimed in claim 19, which comprises a device for activating the metering slide of the integrated metering device of a pharmaceutical powder cartridge moving it at least from a filling position into an emptying position and a securing device for preventing the metering slide from returning into the filling position before the medicament dose is removed from the inhaler.

21. The inhaler for powdered medicaments as claimed in claim 20, wherein the inhaler also comprises a safety device which largely prevents the formation of an air stream for the removal of the medicament if the metering slide has not yet completely reached the emptying position.

22. The inhaler as claimed in claim 19, characterized by a device for reading, from outside the inhaler, the display device of a pharmaceutical powder cartridge, which has been inserted into the inhaler.

23. The inhaler as claimed in claim 19, wherein the visual display devices and the device for reading the display device of a pharmaceutical powder cartridge, which has been inserted into the inhaler are arranged on that side of the inhaler on which a mouthpiece for inhaling the air stream with the medicament is also located.

24. The inhaler as claimed in claim 19, wherein the visual display devices and the device for reading the display device of a pharmaceutical powder cartridge, which has been inserted into the inhaler are arranged on the inhaler in such a way that they are located in the field of vision of a patient when the said patient holds the inhaler in its position of use for inhaling.

25. The inhaler for powdered medicaments as claimed in claim 19, with flow paths in the inhaler for one or more air streams, a dispersing device for dispersing the powdered medicament and a mouthpiece for inhaling the air stream with the medicament, wherein the flow paths, the dispersing device and the mouthpiece are arranged in such a way that during inhalation out of the inhaler an air stream is formed in which a core air stream containing the dispersed, powdered medicament is surrounded by a surrounding air stream without the addition of medicament.

26. The inhaler as claimed in claim 25, wherein the flow paths comprise a powder duct in which a depression for collecting the pharmaceutical powder metered into the flow paths is formed.

27. The inhaler as claimed in claim 19, having a housing and a mouthpiece, which can be removed from the housing, for inhaling, a receptacle, which can be closed by a lid, for the insertion of a pharmaceutical powder cartridge with metering device integrated therein, and a metering button on the upper side of the housing.

28. The inhaler as claimed in claim 27, in which within the housing and the mouthpiece there are arranged:

a functional carrier with horizontal and a plurality of vertical elements for receiving means which act on a pharmaceutical powder cartridge after its insertion into the powder inhaler and its metering device and a horizontal receiving surface of the functional carrier for the insertable pharmaceutical powder cartridge, the receiving surface having a passage opening which is aligned with the discharge opening of the metering device which is integrated into the pharmaceutical powder cartridge.

29. The inhaler as claimed in claim 27 which also comprises a dispersing device, arranged in the mouthpiece, for dispersing powdered medicament doses, in the air stream which is sucked in through a central opening in the mouthpiece during inhalation, the dispersing device being connected by a powder duct to the passage opening in the supporting surface of the functional carrier and the dispersing device having means in order to branch off from the dispersing air stream fed to the dispersing device a powder-free partial air stream which surrounds, as a surrounding air stream, the air stream which leaves the dispersing device and is charged with powder.

30. The inhaler as claimed in claim 27, which also comprises an impulse transmitter which is coupled to first vertical elements of the functional carrier which are arranged parallel to one another at a distance, for the purpose of supplying a mechanical impulse to an inserted pharmaceutical powder cartridge.

31. The inhaler as claimed in claim 27, which also comprises a metering lever which is coupled to a second vertical element with two side walls of the functional carrier which are arranged parallel to one another at a distance, for the purpose of activating the metering device, integrated into the pharmaceutical powder cartridge, for pharmaceutical powder, parts of the metering button which extend through the housing and whose front ends are coupled to other points of the side walls, arranged parallel to one another at a distance, of the second vertical element of the functional carrier, and there are means which engage on the parts on the metering lever in order to pivot the metering lever about its pivotal center, and there are means for activating the impulse transmitter.

32. The inhaler as claimed in claim 27, which also comprises further elements of the functional carrier which form at the rear end of its horizontal part a valve chamber, with an opening to the rear part of the housing interior, which opening can be closed by a valve flap which is coupled to functional carrier elements, and the valve chamber is connected to the dispersing device via an air duct, and a partial air duct branches off from the air duct to the metering device of the pharmaceutical powder cartridge in order to lead a partial air stream through the metering device to the powder duct, in order to convey a medicament dose out of the metering device into the dispersing device.

33. The inhaler as claimed in claim 32, wherein the valve flap has at its upper edge a shaft with outwardly directed bearing journals which engage in bearing bushes on functional carrier elements which form the valve chamber walls, and in the shaft there is a recess with a blocking edge, and an arm extends upward from the shaft next to the recess, at the end of which arm a hook with a blocking edge is constructed.

34. The inhaler as claimed in claim 32, wherein the second vertical element of the functional carrier is a shaft with two side walls whose inner cross section is matched to the outer contour of the pharmaceutical powder cartridge to be inserted, and, between the side walls of the shaft and the side walls of the pharmaceutical powder cartridge, there is still space for the metering lever and the parts of the metering button.

35. The inhaler as claimed in claim 32, wherein the dispersing device has a chamber which is formed by a baffle plate as front wall, a plate as rear wall and an outer wall of the chamber arranged between them, the outer wall diameter of said chamber being smaller than the inner diameter of the mouthpiece surrounding the dispersing device, so that an annular space surrounding the chamber is constructed within the mouthpiece and the outer wall of the chamber is divided into webs by a plurality of slits which extend tangentially into the chamber interior, the outer diameter of the baffle plate is larger than the outer diameter of the chamber so that its edge fits tight against the inside of the mouthpiece, the baffle plate has in the center an outlet opening from which an outlet duct extends through a truncated cone-shaped connector element which is attached on the front side of the baffle plate, and in the edge region of the baffle plate there are a plurality of passage openings which are distributed symmetrically over the circumference and through which powder-free air can pass out of the annular space into the space in front of the baffle plate, the front end of the powder duct which starts at the rear of the baffle plate is connected to one of the slits in the outer and of the chamber and the rear end of the powder duct which extends to below the supporting surface is constructed so as to be fixable in a vertical element of the functional carrier, which vertical element extends downward as far as the inner wall of the housing.

36. The inhaler as claimed in claim 35, wherein the surface, which faces the interior of the chamber, of each of the webs which form the outer wall of the chamber is constructed as a continuous extension of the slit wall so that the chamber has a polygonal cross section.

37. The inhaler as claimed in claim 32, wherein the first vertical elements of the functional carrier are arms which extend upward from the horizontal part of the functional carrier behind the supporting surface, having bearing bushes at their upper ends, and the impulse transmitter has a lever with a hammer element, extending in the direction of the longitudinal axis of the powder inhaler, at the lower end with a shaft at the upper end, the outwardly directed journals of which shaft engage in the bearing bushes in the arms, and in the lower part of the lever there is a laterally offset, upwardly extending transverse spring element which cannot be deflected in the direction of movement of the impulse transmitter but rather transversely thereto, and a drive spring which extends upward from the lower part is molded onto the impulse transmitter.

38. The inhaler as claimed in claim 37, wherein there is a projection with an oblique surface on the transverse spring element of the impulse transmitter on the side facing away from the lever.

39. The inhaler as claimed in claim 37, wherein a drive device is arranged between the housing wall and a side wall of the shaft, having means for activating the display device which is integrated into the upper edge of the pharmaceutical powder cartridge for medicament doses removed from the pharmaceutical powder cartridge.

40. The powder inhaler as claimed in claim 39, wherein the means for activating the display device are a toothed wheel which engages in the display device and which is mounted on a journal which protrudes from the upper edge of the housing, which toothed wheel is driven by a toothed pinion, connected to a toothed transportation wheel, with a smaller number of teeth, the toothed pinion being mounted through an oval opening in the lateral surface of the metering lever in a bearing hole in a lateral surface of the shaft of the functional carrier.

41. The inhaler as claimed in claim 32, wherein the parts of the metering button are two parallel rockers, the distance between which is slightly larger than the width of the pharmaceutical powder cartridge so that during insertion the pharmaceutical powder cartridge can be pushed through the space between the rockers and the front ends of the rockers are connected to one another by means of a bridge, from which bearing journals extend on both sides in bearing bushes in the third vertical elements, and the bridge on the front side has a step bearing for receiving a restoring spring whose other end is supported in a bearing on the rear of the vertical plate of the functional carrier.

42. The inhaler as claimed in claim 32, wherein the means on the rockers of the metering button are driver journals on the outside of both rockers for engaging on the metering lever and a projection which extends upward from the other rocker, the projection projecting beyond the rocker also on the inside in order to activate the impulse transmitter, and the distance between the driver journals and the pivotal center of the metering button being smaller than the distance from the projection so that the engagement of the projection on the transverse spring element of the impulse transmitter takes place with a smaller degree of pressing in of the metering button than the engagement of the driver journal on the metering lever and the further movement of the metering lever up until the engagement of the driver journal releases the engagement of the projection on the transverse spring element of the impulse transmitter.

43. The inhaler as claimed in claim 33, wherein the metering lever has two lateral surfaces at a distance from one another, the ends of which lateral surfaces are connected to one another by bridges forming a ring which engages around the pharmaceutical powder cartridge at a distance, and bearing journals extend outward from the lateral surfaces in their upper regions in bearing bushes in the side walls of the shaft so that the metering lever is pivotably mounted in the longitudinal direction of the powder inhaler, and a lateral surface has an obliquely downwardly running stop edge for the driver journal of the metering button and the metering lever has means for engaging in the metering device integrated into the lower part of the powder cartridge, and there are means for locking the blocking edge of the recess in the shaft of the valve flap and for locking the blocking edge of the hook on the arm which extends upward from the shaft next to the recess, in order to make it possible to lock the metering lever in a center position, differing from its initial position, and in a limit position.

44. The inhaler as claimed in claim 43, wherein the metering lever has on one of its lateral surfaces a lug for hooking in a restoring spring, and the other end of the restoring spring is fixed to a hook which is arranged on a horizontal element of the functional carrier, which element forms the top of the valve chamber, and the force of the restoring spring is not sufficient to release the locking of the metering lever in the center position and limit position but is sufficient to pull back the metering lever into the initial position after the limit locking is released.

45. The inhaler as claimed in claim 43, wherein the means on the metering lever for engaging in the metering device are fingers which extend from arms which are offset laterally into the ring against the lateral surface and extend downward, directed toward one another, through recesses in the side shafts of the metering slide duct into recesses in the side edges of a metering slide which is arranged so as to be capable of moving forward and backward in the metering slide duct of the metering device.

* * * * *